United States Patent [19]

Stransky et al.

[11] Patent Number: 4,900,729

[45] Date of Patent: Feb. 13, 1990

[54] THIENO-1,4-DIAZEPINES

[75] Inventors: Werner Stransky; Karl-Heinz Weber, both of Gau-Algesheim; Gerhard Walther, Bingen; Albrecht Harreus, Ingelheim am Rhein; Jorge C. Stenzel, Mainz; Gojko Muacevic, Ingelheim am Rhein; Wolf-Dietrich Bechtel, Appenheim, all of Fed. Rep. of Germany

[73] Assignee: Boehringer Ingelheim KG, Ingelheim am Rhein, Fed. Rep. of Germany

[21] Appl. No.: 255,903

[22] Filed: Oct. 11, 1988

Related U.S. Application Data

[63] Continuation of Ser. No. 5,992, Jan. 21, 1987, abandoned.

[30] Foreign Application Priority Data

Jan. 21, 1986 [DE] Fed. Rep. of Germany ....... 3601557
Jul. 22, 1986 [DE] Fed. Rep. of Germany ....... 3624646

[51] Int. Cl.$^4$ .................... A61K 31/55; C07D 513/14
[52] U.S. Cl. ...................................... 514/220; 540/560
[58] Field of Search .......................... 540/560; 514/220

[56] References Cited

FOREIGN PATENT DOCUMENTS 3435973 4/1968 Fed. Rep. of Germany ...... 540/560
2405682 8/1974 Fed. Rep. of Germany ...... 540/560
612972 8/1979 Switzerland ........................ 540/560

Primary Examiner—Robert T. Bond

Attorney, Agent, or Firm—D. E. Frankhouser; Mary-Ellen M. Timbers; Alan R. Stempel

[57] ABSTRACT

The invention relates to new thieno-1,4-diazepines of general formula

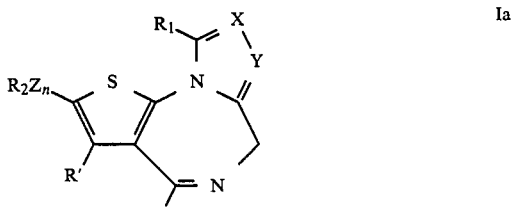

Ia

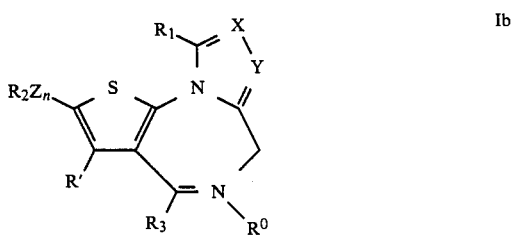

Ib wherein $R_1$, $R_2$, $R_3$, $R°$, $R'$, Z, X, Y and n have the meanings given in the specification.

The new compounds are intended to be used in the treatment of pathological conditions and diseases in which PAF (platelet activating factor) is implicated.

6 Claims, No Drawings

THIENO-1,4-DIAZEPINES

This is a continuation of application Ser. No. 005,992, filed January 21, 1987, now abandoned.

The invention relates to new thieno-1,4-diazepines, the preparation thereof by known methods and their use a pharmaceuticals and as intermediate products. The new thieno-1,4-diazepines correspond to general formula

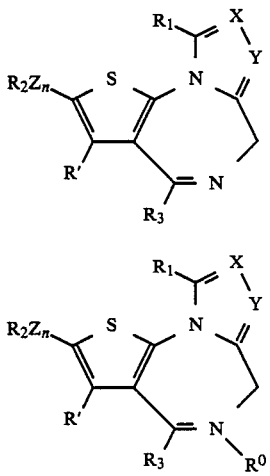

wherein
$R_1$ represents hydrogen, a branched or unbranched alkyl group with 1 to 4 carbon atoms which may optionally be substituted by hydroxy or halogen, a cyclopropyl group, a branched or unbranched alkoxy group with 1 to 4 carbon atoms, preferably methoxy, or a halogen, preferably chlorine or bromine;
when $n > 0$
$R_2$ represents halogen, hydroxy,

wherein
$R_4$ and $R_5$, which may be identical or different, represent hydrogen, a branched or unbranched alkyl, alkenyl or alkynyl group with 1 to 10 carbon atoms which may optionally be substituted by halogen, hydroxy or a C-linked heterocyclic group, whilst the carbon chain may be interrupted by nitrogen, oxygen or sulphur, a branched or unbranched alkylcarbonyl group with 1 to 6 carbon atoms, optionally substituted by hydroxy or halogen, preferably chlorine, or substituted by an amino group which is optionally mono- or disubstituted by a branched or unbranched alkyl group with 1 to 6 carbon atoms, whilst the alkyl group may be substituted by halogen or hydroxy, an optionally substituted arylcarbonyl group, preferably phenylcarbonyl, an optionally substituted arylsulphonyl group, preferably phenylsulphonyl or tolysulphonyl, an alkylsulphonyl group with 1 to 4 carbon atoms, or $R_4$ and $R_5$ together with the nitrogen atom form a saturated or unsaturated 5-, 6- or 7-membered ring optionally mono- or polysubstituted by branched or unbranched alkyl groups with 1 to 4 carbon atoms, this ring possible containing nitrogen, oxygen or sulphur as further heteratoms, whilst each additional nitrogen atom may optionally be substituted by a branched or unbranched alkyl group with 1 to 4 carbon atoms, preferably methyl;

$R_2$ represents an aryl sulphonyloxy group, preferably tolylsulphonyloxy or phenylsulphonyloxy, optionally mono- or polysubstituted by branched or unbranched alkyl and/or alkoxy groups with 1 to 4 carbon atoms;

$R_2$ represents a branched or unbranched alkylsulphonyloxy group with 1 to 4 carbon atoms;

$R_2$ an arylcarbonyloxy group, preferably phenylcarbonyloxy, optionally mono- or polysubstituted by branched or unbranched alkyl and/or alkoxy groups with 1 to 4 carbon atoms;

$R_2$ represents a branched or unbranched alkylcarbonyloxy group with 1 to 12, preferably 1 to 8, carbon atoms, whilst the alkyl chain may be interrupted by nitrogen, oxygen or sulphur;

$R_2$ represents

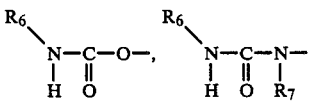

wherein $R_6$ represents a branched or unbranched alkyl, alkenyl or alkynyl group with 1 to 4 carbon atoms, optionally substituted by halogen, an aryl group optionally mono- or polysubstituted by branched or unbranched alkyl and/or alkoxy groups with 1 to 4 carbon atoms, $R_7$ represents hydrogen or a branched or unbranched alkyl group with 1 to 4 carbon atoms;

$R_2$ represents

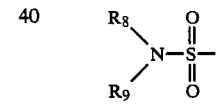

wherein $R_8$ and $R_9$, which may be identical or different, represent a branched or unbranched alkyl group with 1 to 4 carbon atoms, or $R_8$ and $R_9$ together with the nitrogen atom represent a 5-, 6- or 7-membered ring optionally mono- or polysubstituted by branched or unbranched alkyl groups with 1 to 4 carbon atoms, this group optionally containing a further heteroatoms nitrogen, oxygen or sulphur, whilst each additional nitrogen atom is substituted by an alkyl group with 1 to 4 carbon atoms, preferably methyl;

$R_2$ represents a branched or unbranched alkoxy group with 1 to 4 carbon atoms; an aryloxy group, preferably phenyloxy or substituted phenyloxy;

$R_2$ represents an imido group; dioxolan, substituted dioxolan;

when n is greater than or equal to 0
$R_2$, where n is greater than or equal to 0, represents —CH=O; =COOH, cyano;

$R_2$ represents a branched or unbranched alkoxycarbonyl group with 1 to 4 carbon atoms, with the proviso that if R' represents hydrogen, $R_3$ represents o-chlorophenyl, X and Y both represent nitrogen, $R_2Z_n$ cannot represent methoxycarbonylethyl;

R₂ represents an aryloxycarbonyl group, preferably phenyloxycarbonyl;

R₂ represents a group of general formula

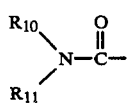

wherein R₁₀ and R₁₁, which may be identical or different, represent hydrogen, phenyl, substituted phenyl, a branched or unbranched alkyl, alkenyl or alkynyl group with 1 to 10 carbon atoms, which may optionally be substituted by halogen, hydroxy, nitro, amino, substituted amino or, if R₁₀=hydrogen or alkyl and Y=C—R₁ or Y represents nitrogen and X represents C-alkyl, R₁₁ may be substituted by an ester function or an acid amide of general formula

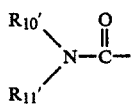

wherein

R'₁₀ and R'₁₁ have the same meanings as R₁₀ and R₁₁, with the exception of an acid amide, R₁₀ or R₁₁ represent a saturated or unsaturated 5-, 6- or 7-membered heterocyclic ring linked by a carbon atom, optionally mono- or polysubstituted by branched or unbranched alkyl with 1 to 4 carbon atoms, R₁₀ and R₁₁ together with the nitrogen atom represent a saturated or unsaturated 5-, 6- or 7-membered ring optionally mono- or polysubstituted by branched or unbranched alkyl groups with 1 to 4 carbon atoms and optionally containing, as further heteroatoms, nitrogen, oxygen or sulphur, whilst each additional nitrogen atom may be substituted by a branched or unbranched alkyl group with 1 to 4 carbon atoms, preferably methyl, with the proviso that if X, Y both represent nitrogen, R' represents hydrogen, Z represents an unbranched alkyl chain with n carbon atoms and (a)
R₃=o-chlorophenyl and
R₁=methyl and n=0, 1, 2, 3 or 4 NR₁₀R₁₁ does not represent morpholino, or
n=0 or 1
NR₁₀R₁₁ does not represent amino, or
n=2
NR₁₀R₁₁ does not represent diethylamino, methylamino, isopropylamino, dimethylamino, cyclopropylamino, piperidino, pyrrolidino, cyclohexylamino, N'-methylpiperazino, amino, di(hydroxyethylamino) or hydroxyethylamino, or (b)
R₃=o-chlorophenyl and
R₁=chloromethyl, bromomethyl, propyloxy, hydrogen, methoxy, bromine or cyclopropyl, and
n=2
NR₁₀R₁₁ does not represent morpholino, or (c)
R₃=o-chlorophenyl
and R₁=cyclopropyl and
n=2
NR₁₀R₁₁ does not represent diethylamino, or n=8
NR₁₀R₁₁ does not represent morpholino or (d)
R₃=phenyl,
R₁=methyl,
n=2
NR₁₀R₁₁ does not represent morpholino (e)
R₃=2-nitrophenyl, 2-methylphenyl, 2-trifluoromethyl,
R₁=methyl
n=2
NR₁₀R₁₁ does not represent morpholino, (f)
R₃=2-chlorophenyl,
R₁=methoxy
n=2
NR₁₀R₁₁ does not represent diethylamino or piperidino, (g)
R₃=2-chlorophenyl,
R₁=methoxy,
n=2,
NR₁₀R₁₁ does not represent N'-methylpiperazino;

R₂ represents a group of general formula

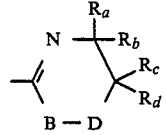

wherein

B represents oxygen, sulphur, NH or NC₁-C₆-alkyl

D represents the group (C Re Rf)n, wherein n may be from 0 to 3,

Ra represents hydrogen, alkyl with 1 to 6 carbon atoms optionally substituted by a hydroxy or amino group, C₁ to C₄ alkoxycarbonyl, dialkylaminocarbonyl, Rb, Rc, Rd, Re, Rf represent hydrogen, alkyl with 1 to 6 carbon atoms optionally substituted by a hydroxy or amino group, or phenyl;

R₃ represents phenyl, wherein the phenyl ring, preferably in the 2 position, may be mono-or poly-substituted by methyl, preferably halogen, most particularly chlorine or bromine, nitro, alkoxy, preferably methoxy and/or trifluoromethyl, or R₃ may represent pyridyl;

R* represents hydrogen, alkyl or an acyl group with 1 to 4 carbon atoms in the alkyl chain, preferably acetyl;

R' represents hydrogen, phenyl, substituted phenyl or a branched or unbranched alkyl group with 1 to 4 carbon atoms, preferably methyl;

X,Y independently of each other represent C—R₁ or N but cannot both simultaneously represent C—R₁, or Y represents the group C—COOR*, wherein R*=alkyl or hydrogen and X=nitrogen;

Z represents a branched or unbranched alkyl or alkenyl group with n carbon atoms, wherein Z may optionally additionally be substituted by aryl, preferably phenyl or substituted phenyl, or disubstituted by R₂, whilst R₂ may be identical or different; and n represents one of the numbers 0, 1, 2, 3, 4, 5, 6, 7, 8, 9 or 10, in the form of their racemates, enantiomers, diastereomers and mixtures thereof, as free bases or as the physiologically acceptable acid addition salts thereof.

Preferred compounds are the compounds of general formulae Ia and Ib
wherein
$R_1$ represents methyl, ethyl, methoxy, ethoxy or halogen, preferably chlorine or bromine;
$R_2$ represents chlorine, bromine, iodine or hydroxy,

wherein
$R_4$ and $R_5$, which may be identical or different, represent hydrogen, a branched or unbranched alkyl group with 1 to 6, more particularly 1 to 4, carbon atoms, whilst the carbon chain may be interrupted by nitrogen, a branched or unbranched alkylcarbonyl group with 1 to 4 carbon atoms, optionally substituted by a dimethylamino group, a phenylcarbonyl group, when $R_5$=hydrogen, $R_2$ may also represent a phenylsulphonyl group optionally substituted by acylamino, particularly acetylamino, amino, alkylamino or dialkylamino, or
$R_4$ and $R_5$ together with the nitrogen atom form a piperidine, pyrrolidine, N'-methylpiperazine, an optionally dimethyl-substituted morpholine ring, a pyrrole, pyrazole, imidazole or triazole ring;
$R_2$ represents —CH=O; —COOH; a $\Delta^2$-imidazoline, -oxazoline, -thiazoline optionally mono- or polysubstituted by methyl; a tolylsulphonyloxy group; a methylsulphonyloxy group; a phenylcarbonyloxy group; a branched or unbranched alkylcarbonyloxy group with 1 to 5 carbon atoms; a methoxy- or ethoxycarbonyl group;
$R_2$ represents

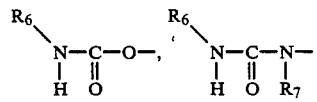

wherein $R_6$ represents a branched or unbranched alkyl group with 1 to 4 carbon atoms, $R_7$ represents hydrogen or a branched or unbranched alkyl group with 1 to 4 carbon atoms;
$R_2$ represents

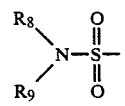

wherein $R_8$ and $R_9$, which may be identical or different, represent a methyl, ethyl, propyl or isopropyl group or $R_8$ and $R_9$ together with the nitrogen atom represent an N'-methylpiperazine or morpholine ring;
$R_2$ represents

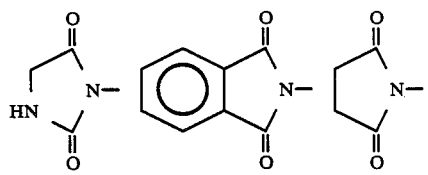

$R_3$ represents phenyl, whilst the phenyl ring may be substituted by halogen, preferably chlorine, preferably in the 2 position.
R* represents hydrogen, methyl or acetyl;
R' represents hydrogen;
X,Y independently of each other represent C—$R_1$ or N but cannot both simultaneously represent C—$R_1$, ($R_1$ represents preferably hydrogen, or Y represents the group C—COOR*, wherein R*=alkyl or hydrogen, and X=nitrogen;
Z is defined as hereinabove and preferably represents —(CH$_2$)$_n$—, optionally substituted by phenyl or disubstituted by $R_2$, whilst $R_2$ may also be different, or —CH$_2$—CHR$_2$—CH$_2$—R$_2$, —CH$_2$—CHR$_2$R$_2$, —CH$_2$CHR$_2$—CH$_2$—C$_6$H$_5$; and
n represents one of the numbers 1, 2, 3, 4, 5, 6, 7, 8, 9 or 10, and optionally the physiologically acceptable acid addition salts thereof.

Particularly preferred compounds are compounds of general formula Ia wherein $R_1$=methyl or methoxy, $R_3$=o-chlorophenyl, R' represents hydrogen, X and Y both represent nitrogen, or X represents CH and Y represents nitrogen, Z represents (CH$_2$)$_n$, n=2, 3 or 7 and $R_2$ and R* are as hereinbefore defined.

Unless otherwise stated, halogen represents one of the atoms fluorine, chlorine, bromine or iodine, whilst the term aryl groups indicates optionally mono- or polysubstituted aromatic groups with up to 10 carbon atoms in the ring system, such as phenyl, pyridyl, thienyl, furyl or naphthyl, the phenyl ring being preferred.

The terms alkyl, alkenyl, alkynyl and alkoxy groups indicate, unless otherwise stated, branched or unbranched, optionally substituted groups with 1 to 8 carbon atoms in the carbon chain.

Suitable substituents include one or more atoms from the group comprising halogen, methyl, methoxy, hydroxy or trifluoromethyl.

Preferred imido groups are the following structures:

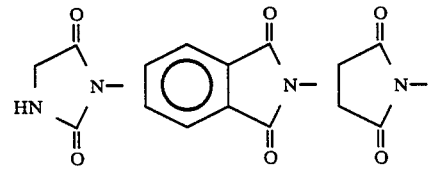

Unless otherwise stated, terms lower alkyl and lower acyl refer to branched or unbranched groups having 1 to 4 carbon atoms in the alkyl chain.

In the general formulae, "n" in "$Z_n$" indicates the number of carbon atoms in the alkyl or alkenyl chain. If $Z_n$ is disubstituted by $R_2$, the substituents may be identical or different. If $Z_n$ is a branched alkyl or alkenyl group, the branching is preferably in the $\alpha$ or $\beta$ position with respect to the terminal functional group.

The term alkenyl denotes alkyl chains with at least one double bond, whilst alkynyl denotes alkyl chains with at least one triple bond.

Unless otherwise stated, the preferred alkyl groups are: methyl, ethyl, propyl, isopropyl, n-butyl, isobutyl and t.butyl, the methyl groups being particularly important. The preferred alkoxy group is methoxy.

The new compounds of general formula Ia may be obtained by known methods from the corresponding thienodiazepinethiones of general formula II or by varying functional groups in the side chain of the hetrazepine structure already prepared.

The new compounds of general formula Ib are obtained by reducing compounds of general formula Ia. The reaction is carried out with known reducing agents in organic solvents, e.g. with zinc in a mixture of glacial acetic acid and an inert organic solvent, such as halogenated hydrocarbons, e.g. dichloromethane, at temperatures of between ambient temperature and the boiling point of the reaction mixture or, for example, using lithium aluminium hydride (if $R_2$ is not reduced).

Compounds of general formula Ib wherein R* represents an alkyl or acyl group may be prepared from the above-mentioned compounds by alkylation or acylation by known methods.

Compounds of general formula Ia

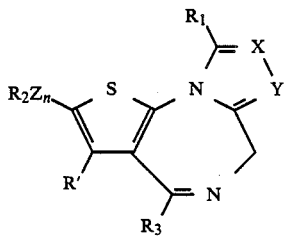

wherein $R_2$ represents an ester grouping —COOR* as defined hereinbefore, preferably R*32 lower alkyl, more preferably methyl and ethyl, or $R_2$=OH, preferably protected as an acetic acid ester, are pharmacologically active and at the same time important intermediate compounds for the preparation of further $R_2$-functionalised hetrazepines of general formula Ia or Ib.

Compounds of general formula Ia with $R_2$—COOR* are also referred to hereinafter as formula I.

Compounds of general formula Ia with a triazole ring condensed thereon may be prepared in the usual way from the corresponding thieno-1,4-diazepinethiones of general formula

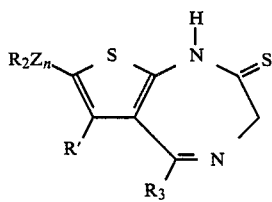

($R_2$=—COOR* (preferably R*=lower alkyl) or $R_2 Z_n$ represents a methyl or ethyl alkyldicarboxylate with 1 to 10 carbon atoms in the alkyl chain or $R_2$=OCOCH$_3$ or SO$_2$ NR$_8$R$_9$).

For this purpose a compound of formula II may either (a) be reacted with an acid hydrazide of general formula

$R_1$—CONHNH$_2$,     III or (b) be converted with hydrazine into a compound of general formula

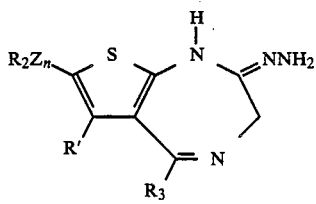

and subsequently reacted with an acid halide, preferably an acid chloride, of general formula $R_1$—COHal     V or with an orthoester of general formula

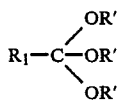

wherein R' represents a lower alkyl group, preferably methyl or ethyl.

The reaction of the thione II with an acid hydrazide III according to process (a) is carried out in an inert organic solvent such as dioxan, dimethylformamide, tetrahydrofuran or a suitable hydrocarbon such as benzene or toluene at temperatures of between ambient temperatures and the boiling point of the reaction mixture. The end products are isolated by known methods, e.g. by crystallisation.

The reaction of the thione II with hydrazine according to process (b) is carried out in inert organic solvents such as tetrahydrofuran, dioxan, halogenated hydrocarbons, such as methylene chloride, suitable hydrocarbons, at temperatures of between ambient temperature and the boiling point of the reaction mixture.

The hydrazin-1,4-diazepines thus produced may be isolated by conventional methods or further processed directly.

Further reaction with an acid halide V or an orthoester VI is carried out in an inert organic solvent such as halogenated hydrocarbons or cyclic or aliphatic ethers, but may also be carried out directly in substance. The end product Ia is isolated by known methods, for example by crystallisation.

The hetrazepines of general formula Ia wherein X represents a CH group and Y represents nitrogen are synthesised in known manner from the thione of general formula II by reacting with an aminoalkyne of general formula VII wherein $R_{11}$ represents hydrogen or an alkyl group, preferably hydrogen, whilst the use of hydrochlorides for the hetrazepine cyclisation makes it possible to obtain $R_2$ groups susceptible to hydrolysis.

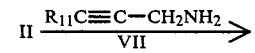

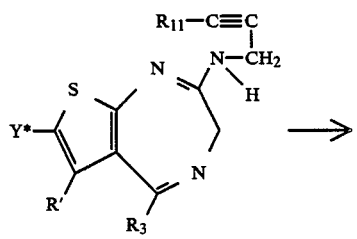

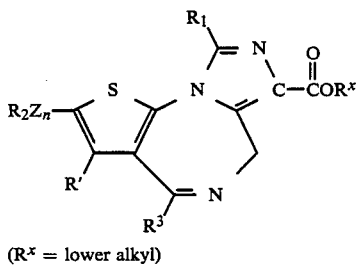

($R^x$ = lower alkyl)

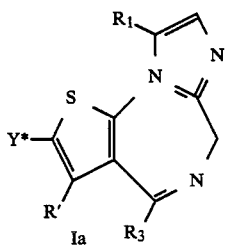

$Y^* = R_2Z_n-$

Using this method it is possible to prepare compounds of general formula Ia wherein $R_1$ represents an alkyl, preferably a methyl group.

Another method is to react the thione of general formula II with an α-aminoaldehyde-alkylacetal or α-aminoketone-alkylketal of general formula VIII according to the following synthesis plan

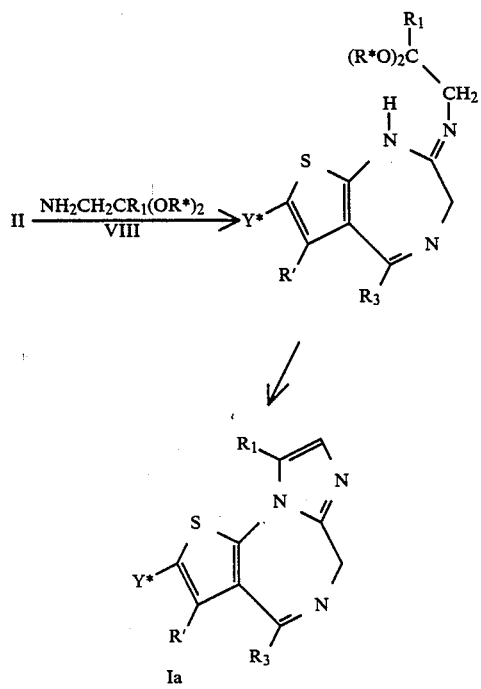

$Y^* = R_2Z_n-$ wherein $R_1$ represents hydrogen or an alkyl group with 1 to 4 carbon atoms or a cyclopropyl group and $R^*$ represents a lower alkyl group.

Analogous methods for synthesising an acetal or ketal of general formula VIII and an analogous method of cyclisation are described in Swiss Pat. No. 580 099.

Compounds of general formula Ia wherein X represents nitrogen and Y represents CH may be obtained by decarboxylation of compounds of general formula Compounds of general formula Ic are obtained, for example, from the diazepinethiones of general formula II by reacting with isocyanoacetates.

Analogous methods for the preparation of suitable compounds of general formula Ic are described, for example, in Dutch patent application No. 78 03 585.

Compounds of general formula Ia which contain a [1,5-a]-linked imidazole ring may also be obtained, for example, by methods analogous to those described in DE-OS 25 40 522.

Compounds of general formula Ia wherein $R_1$ represents chlorine or bromine are prepared from compounds wherein $R_1$=hydrogen by reacting with chlorine or bromine in pyridine.

The corresponding alkoxy compounds are obtained, for example, from one of the above-mentioned chlorine or bromine compounds by reaction with the corresponding alkoxide.

However, preferably, the groups $R_1$ representing halogen and alkoxy are only inserted after the synthesis of the fully functionalised hetrazepine of general formula Ia by the method described.

The methods of preparing compounds of general formula I or Ia described above start from the thione of general formula II wherein the functional group $R_2$ is not attacked under the reaction conditions used or may be protected by suitable protecting groups. This applies particularly when $R_2$ is an ester function, an alkylcarbonyloxy group, dioxolan, substituted dioxolan or when $R_2 = R_8R_9NSO_2-$.

Thus, diazepine thiones of general formula II may be prepared as follows.

Analogously to the method described by Gewald et al. Chem. Ber. 98, 3571 (1965), ibid 99, 94 (1966), the functionalised thienes c are obtained, starting from the correspondingly functionalised aldehydes or ketones of general formula a by reacting with the corresponding acetophenone b. Using known methods, these thienes c are converted by bromoacetylation and subsequent reaction with ammonia into the cyclised, 1,4-diazepinones which are subsequently converted with phosphorus pentasulphide or Lawesson's Reagent$^R$ into the thione of general formula II.

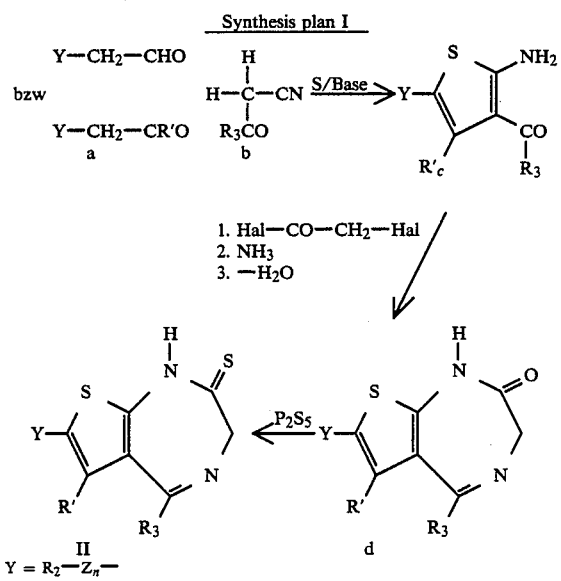

Synthesis plan I

Preferably, $R_2$ represents a carboxylic acid ester such as a methyl or ethyl carboxylate, or an alkylcarbonyloxy group or an aminosulphonyl group. The ω-functionalised aldehydes a required for the preparation may be obtained, for example, by reductive ozone cleaving of cyclic enol ethers (L. Claisen, Ber. dtsch. chem. Ges. 40, 3907 and V. Schmid and P. Grafen, Liebigs Ann. Chem. 656, 97 (1962), suitably fatty acid derivatives such as oleyl acetate or suitable unsaturated heterocyclic groups. Ozonisation is preferably carried out in methylene chloride or ethyl acetate at −78° C. to +20° C., preferably between −40° C. and −20° C.

Another method of preparation is illustrated in the following reaction plan:

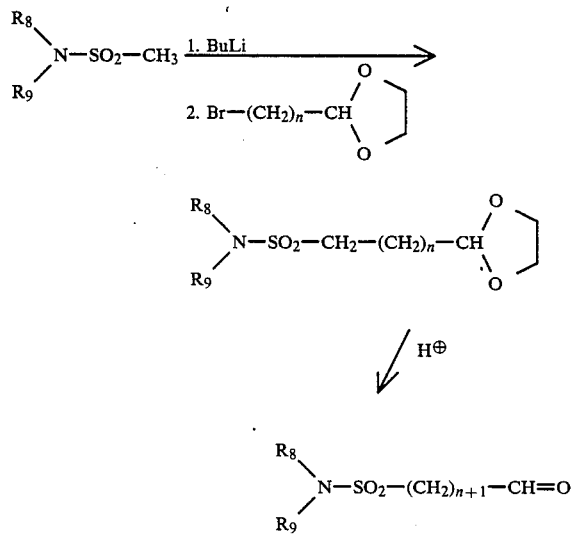

The reaction of the aldehydes a leads to the aminothiophene derivatives c in known manner, as shown in synthesis plan 1, according to K. Gewald et.al., Chem. Ber. 98, 3571 (1965) and Chem. Ber. 99, 94 (1966).

The 2-haloacetylaminothiophene derivatives formed diazepinone d which is subsequently reacted with phosphorus pentasulphide or Lawesson's Reagent$^R$ to form the thione of general formula II.

If $Z_n$ is a branched alkyl or alkenyl group, optionally substituted by aryl, preferably phenyl, or if $Z_n$ is disubstituted by $R_2$, the branching may be synthesised at the stage of the ω-functionalised aldehyde or after the preparation of the fully synthesised hetrazepine, using known methods.

If $Z_n$ is di-functionalised, the functional groups may be linked to the same carbon atom or to different carbon atoms.

The carboxylic acid esters ($R_2$=COOR*, R*=lower alkyl) of general formula Ia are valuable starting compounds I for the introduction of other functional groups.

Starting from the esters, the corresponding carboxylic acids of general formula Ia may be obtained by saponification, e.g. in alcoholic aqueous potassium hydroxide solution, e.g. with KOH in ethanol, at temperatures between ambient temperature and the boiling point of the reaction mixture.

Carboxylic acid amides of general formula Ia may be prepared by known methods, e.g. from the corresponding carboxylic acids or the carboxylic acid equivalents thereof by reacting with a primary or secondary amine or ammonia of general formula

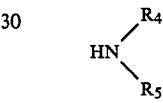

Conversion into a carboxylic acid chloride or acid anhydride or reaction of the acid in the presence of carbonyldiimidazole, sulphonyldiimidazole or cyclohexylcarbodiimide are preferred.

The reaction of the free acid with the amine is effected in the presence of a carbodiimide, e.g. cyclohexylcarbodiimide, carbonyldiimidazole or sulphonyldiimidazole in an inert solvent such as dimethylformamide, tetrahydrofuran, dioxan or halogenated hydrocarbon at temperatures of between 0° C. and the boiling point of the reaction mixture.

For the reaction of the amine with an acid halide or acid anhydride, the amine is reacted with the acid halide or acid anhydride in an inert solvent, for example dimethylformamide, tetrahydrofuran, dioxan or a suitable hydrocarbon such as toluene at temperatures of between ambient temperature and the boiling point of the reaction mixture, optionally with the addition of an acid-binding agent such as sodium carbonate, sodium bicarbonate or a tertiary organic base, e.g. pyridine or triethylamine.

If the amine is a liquid the reaction may also be carried out in an excess of the amine without any additional solvent.

The acid halide or acid anhydride is obtained from the free acid in conventional manner, e.g. by reacting the acid with a thionyl halide or by reacting an alkali metal salt of the acid with acetylchloride or chloroformic acid chloride.

Instead of the reaction with an amine it is also possible to carry out the reaction with an amino acid derivative.

Esters of general formual Ia, particularly the methyl or ethyl esters, may be converted into the corresponding alcohol by selective reduction of the ester function. The reaction is carried out with inverse addition of the reducing agent such as lithium alanate or sodium borohydride (inverse activation), under generally conventional reaction conditions, e.g. in inert organic solvents, e.g. ethers, tetrahydrofuran at temperatures of between ambient temperature and the boiling point of the reaction mixture.

Carbamates or ureas of general formula Ia wherein $R_2 = R_6NHCOO-$ or $R_6NHCONR_7-$ are obtained from the reaction of the corresponding alcohols or amines with the desired isocyanate in organic solvents such as tetrahydrofuran, methylene chloride, at temperatures of between ambient temperature and the boiling point, preferably at elevated temperatures, of the reaction mixture with the addition of base, preferably DABCO (1,4-diazabicyclo(2,2,2)octane).

Compounds wherein $R_2$ is alkylcarbonyloxy or arylcarbonyloxy are obtained from the corresponding alcohols of general formula Ia by reacting with an acid equivalent derived from a carboxylic acid of general formula

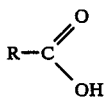

wherein R represents an aryl group or preferably a branched or unbranched alkyl group with 1 to 8 carbon atoms, whilst the carbon chain may be interrupted by nitrogen, oxygen or sulphur. The same reaction conditions may be used as in the preparation of the acid amides.

From the carboxylic acids of general formula Ia wherein $R_2 = COOH$ it is possible to prepare the carboxyl azides by known methods; these can then be converted in an inert organic solvent such as dioxan into the isocyanantes by Curtius rearrangement. These isocyanates may be converted into the primary amines by generally known methods and into the urethanes and ureas as described above.

Starting from compounds of general formula Ia wherein $R_2 = OH$, compounds of general formula Ia wherein $R_2$ represents an alkyl- or arylsulphonyloxy group are obtained by reacting with alkyl- or arylsulphonic acid halides. The reaction is carried out in inert organic solvents such as methylene chloride with sulphonic acid halides with the addition of acid binders such as triethylamine.

The mesylates thus obtained are good leaving groups and can be exchanged nucleophilically. Correspondingly functionalised compounds of general formula Ia, for example $R_2 = CH_3SO_3-$, may be reacted with primary or secondary amines of formula

or an imido group, e.g. phthalimide. Compounds of general formula Ia are obtained wherein $R_2$ contains the group $NR_4R_5$ or an imido group.

The reaction is carried out in inert organic solvents such as tetrahydrofuran or dioxan, at between ambient temperature and the boiling point of the reaction mixture, preferably at elevated temperatures.

Starting from the above-mentioned mesylates, compounds of general formula Ia are obtained wherein $R_2$ represents an aryloxy or alkoxy group by reacting with the corresponding alkoxides, either in an excess of alcohol as solvent or in inert solvents, e.g. dioxan, at between ambient temperature and the boiling point of the mixture of solvents, preferably between 60° and 80° C.

Compounds of general formula Ia wherein $R_2 = NH_2$ are obtained analogously to known methods by cleaving the corresponding phthalimide.

The primary or secondary amines thus obtained may be reacted according to known methods with carboxylic acid equivalents derived from carboxylic acids of general formula

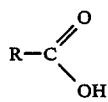

wherein R has the meanings of $R_{10}$, to yield compounds of general formula Ia wherein $R_4$ or $R_5$ represents an alkyl- or arylcarbonyl group. The oxidation of the alcohols yields aldehydes which are shortened by one chain member.

Compounds of general formula Ia wherein $R_2$ represents a heterocyclic group such as an oxazoline, thiazoline or imidazoline are obtained, for example, from the corresponding carboxylic acids of general formula Ia by reacting with a bis-functionalised amine such as an amino alcohol, an aminomercaptan or a diamine, in the presence of triphenylphosphine, carbon tetrachloride and a tertiary organic base in acetonitrile. Analogously the corresponding 6- and 7-membered heterocyclic groups may also be prepared. The reaction is carried out in a temperature range of between 0° C. and the boiling point of the reaction mixture, preferably between 0° C. and ambient temperature. Compounds of general formula Ia wherein $R_2$ indicates an oxazoline group are obtained from the correspondingly hydroxy-functionalised carboxylic acid amines by reaction of cyclisation with thionylchloride in an inert organic solvent such as methylene chloride.

If desired, these may be converted into the corresponding thiazoline by sulphurisation, e.g. with phosphorus pentasulphide or Lawesson's Reagent$^R$.

Compounds of general formula Ia wherein $R_2$ is a cyano group are obtained from the corresponding primary carboxylic acid amides by reacting with phosphorus oxychloride in an inert organic solvent, e.g. dichloroethane, under reflux conditions.

Compounds of general formula Ia wherein $R_2$ is an imidazoline optionally substituted by branched or unbranched alkyl groups may be obtained, starting from compounds Ia wherein $R_2 = CN$, via the imidoethylester hydrochloride by reacting with a diamine (Pinner reaction). The imidoethylester hydrochloride is formed by treating the nitrile with an excess of ethanolic hydrochloric acid. The crystalline crude product obtained is reacted in ethanol with the diamine (e.g. ethylene diamine) first while cooling with ice and then under reflux conditions. In this way, compounds of formula Ia are obtained wherein $R_2$ is an imidazoline-2 group. In the case of N—H, this amino function may be alkylated by known methods.

Compounds of general formula Ia wherein $R_2$ is a halogen atom, e.g. iodine, are obtained from a compound of general formula Ia wherein $R_2$ is a toluenesulphonic acid group by reacting with a corresponding halogenating agent, e.g. NaI, in anhydrous solvents, e.g. acetone.

If the compounds according to the invention contain an asymmetrically substituted carbon atom, they may be resolved by known methods into their optically active enantiomers.

Analogously to known methods or using the methods described above, the following compounds may be prepared, for example:

2-[4-(2-Chlorophenyl)-9-methyl-6H-thieno[3,2-f][1,2,4]-triazolo[4,3-a][1,4]diazepine-2-yl]-ethane-1-sulphonic acid-N-methylpiperazide 3-[4-(2-Chlorophenyl)-9-methyl-6H-thieno-[3,4-f][1,2,4]triazolo[4,3-a][1,4]diazepin-2-yl]-propyl acetate 2-[7-(N'-Methylpiperazinylcarbonyloxy)heptyl]-4-(2-chlorophenyl)-9-methyl-6H-thieno[3,2-f][1,2,4]triazolo[4,3-a][1,4]diazepine 2-[3-(N'-Methylpiperazinylcarbonyloxy)propyl]-4-(2-chlorophenyl)-9-methyl-6H-thieno[3,2-f][1,2,4]triazolo[4,3-a][1,4]diazepine 2-[3-(N-Morpholinylcarbonyloxy)propyl]-4-(2-chlorophenyl)-9-methyl-6H-thieno[3,2-f][1,2,4]triazolo[4,3-a][1,4]-diazepine 2-[7-(N-Morpholinylcarbonyloxy)heptyl]-4-(2-chlorophenyl)-9-methyl-6H-thieno[3,2-f][1,2,4]triazolo[4,3-a][1,4]-diazepine 2-(2-Hydroxyethyl)-4-(2-chlorophenyl)-9-methyl-6H-thieno-3,2-f][1,2,4]triazolo[4,3-a][1,4]diazepine 2-(4-Hydroxybutyl)-4-(2-chlorophenyl)-9-methyl-6H-thieno[3,2-f][1,2,4]triazolo[4,3-a][1,4]diazepine 2-(5-Hydroxypentyl)-4-(2-chlorophenyl)-9-methyl-6H-thieno[3,2-f][1,2,4]triazolo[4,3-a][1,4]diazepine 2-(10-Hydroxydecyl)-4-(2-chlorophenyl)-9-methyl-6H-thieno[3,2-f][1,2,4]triazolo[4,3-a][1,4]diazepine 7-[4-(2-Chlorophenyl)-9-methyl-6H-thieno[3,2-f][1,2,4]triazolo[4,3-a][1,4]diazepin-2-yl]-heptyl acetate 2-(3-Acetoxypropyl)-4-(2-chlorophenyl)-9-bromo-6H-thieno[3,2-f][1,2,4]triazolo[4,3-a][1,4]diazepine 2-[2-(Methylcarbonyloxy)ethyl]-4-(2-chlorophenyl)-9-methyl-6H-thieno[3,2-f][1,2,4]triazolo[4,3-a][1,4]diazepine 2-[4-(Isopropylcarbonyloxy)butyl]-4-(2-chlorophenyl)-9-methyl-6H-thieno[3,2-f][1,2,4]triazolo[4,3-a][1,4]diazepine 2-[5-(Methylcarbonyloxy)pentyl]-4-(2-chlorophenyl)-9-methyl-6H-thieno[3,2-f][1,2,4]triazolo[4,3-a][1,4]diazepine 3-[4-(2-Chlorophenyl)-9-methyl-6H-thieno[3,2-f][1,2,4]triazolo[4,3-a][1,4]diazepin-2-yl]-propyl methane sulphonate 2-[2-(Methylsulphonyloxy)ethyl]-4-(2-chlorophenyl)-9-methyl-6H-thieno[3,2-f[1,2,4]triazolo[4,3-a][1,4]diazepine 2-[4-Methylsulphonyloxy)butyl]-4-(2-chlorophenyl)-9-methyl-6H-thieno[3,2-f][1,2,4]triazolo[4,3-a][1,4]diazepine 2-[5-(Methylsulphonyloxy)pentyl]-4-(2-chlorophenyl)-9-methyl-6H-thieno[3,2-f][1,2,4]triazolo[4,3-a][1,4]diazepine 2-[10-(Methylsulphonyloxy)decyl]-4-(2-chlorophenyl)-9-methyl-6H-thieno[3,2-f][1,2,4]triazolo[4,3-a][1,4]diazepine 2-[3-(N-Morpholinyl)propyl]-4-(2-chlorophenyl)-9-methyl-6H-thieno[3,2-f][1,2,4]triazolo[4,3-a][1,4]diazepine 2-[2-(N-Morpholinyl)ethyl]-4-(2-chlorophenyl)-9-methyl-6H-thieno[3,2-f][1,2,4]triazolo[4,3-a][1,4]diazepine 2-[4-(N-Morpholinyl)butyl]-4-(2-chlorophenyl)-9-methyl-6H-thieno[3,2-f][1,2,4]triazolo[4,3-a][1,4]diazepine 2-[5(N-Morpholinyl)pentyl]-4-(2-chlorophenyl)-9-methyl-6H-thieno[3,2-f][1,2,4]triazolo[4,3-a][1,4]diazepine 2-[10-(2,6-Dimethylmorpholin-4-yl)decyl]-4-(2-chlorophenyl)-9-methyl-6H-thieno[3,2-f][1,2,4]triazolo[4,3-a][1.4]diazepine 2-[3-(N-Morpholinyl)propyl]-4-(4-chlorophenyl)-9-methyl-6H-thieno[3,2-f][1,2,4]triazolo[4,3-a][1,4]diazepine 2-[3-(N-Morpholinyl)propyl]-4-(2,6-dichlorophenyl)-9-methyl-6H-thieno[3,2-f][1,2,4]triazolo[4,3-a][1,4]diazepine 2-[3-(N-Morpholinyl)propyl]-4-(pyridin-b 2-yl)-9-methyl-6H-thieno[3,2-f][1,2,4]triazolo[4,3-a][1,4]diazepine 2-(7-Acetylaminoheptyl)-4-(2-chlorophenyl)-9-methyl-6H-thieno[3,2-f][1,2,4]triazolo[4,3-a][1,4]diazepine 2-(7-N-Phthalimidoheptyl)-4-(2-chlorophenyl)-9-methyl-6H-thieno[3,2-f][1,2,4]triazolo[4,3-a][1,4]diazepine 2-(3-Iodopropyl)-4-(2-chlorophenyl)-9-methyl-6H-thieno[3,2-f][1,2,4]triazolo[4,3-a][1,4]diazepine 2-(7-Aminoheptyl)-4-(2-chlorophenyl)-9-methyl-6H-thieno[3,2-f][1,2,4]triazolo[4,3-a][1,4]diazepine 2-(6-Formylhexyl)-4-(2-chlorophenyl)-9-methyl-6H-thieno[3,2-f][1,2,4]triazolo[4,3-a][1,4]diazepine 2-[2-(Imidazol-1-yl)ethyl]-4-(2-chlorophenyl)-9-methyl-6H-thieno[3,2-f][1,2,4]triazolo[4,3-a][1,4]diazepine 2-[3-(Imidazol-1-yl)propyl]-4-(2-chlorophenyl)-9-methyl-6H-thieno[3,2-f][1,2,4]triazolo[4,3-a][1,4]diazepine 2-[4-(Imidazol-1-yl)-butyl]-4-(2-chlorophenyl)-9-methyl-6H-thieno[3,2-f][1,2,4]triazolo[4,3-a][1,4]diazepine 2-[5-(Imidazol-1-yl)pentyl]-4-(2-chlorophenyl)-9-methyl-6H-thieno[3,2-f][1,2,4]triazolo[4,3-a][1,4]diazepine 2-[7-(Imidazol-1-yl)heptyl]-4-(2-chlorophenyl)-9-methyl-6-H-thieno[3,2-f][1,2,4]triazolo[4,3-a][1,4]diazepine 2-[2-([1,2,4]Triazol-1-yl)ethyl]-4-(2-chlorophenyl)-9-methyl-6H-thieno[3,2-f][1,2,4]triazolo[4,3-a][1,4]diazepine 2-[3-([1,2,4]Triazol-1-yl)propyl]-4-(2-chlorophenyl)-9-methyl-6H-thieno[3,2-f][1,2,4]triazolo[4,3-a][1,4]diazepine 2-[4-([1,2,4]Triazol-1-yl)butyl]-4-(2-chlorophenyl)-9-methyl-6H-thieno[3,2-f][1,2,4]triazolo[4,3-a][1,4]diazepine 2-[5-([1,2,4]Triazol-1-yl)pentyl]-4-(2-chlorophenyl)-9-methyl-6H-thieno[3,2-f][1,2,4]triazolo[4,3-a][1,4]diazepine 2-[2-(4,4-Dimethyloxazolin-2-yl)ethyl]-4-(2-chlorophenyl)-9-methyl-6H-thieno[3,2-f][1,2,4]triazolo[4,3-a][1,4]diazepine 2-[3-(N-Morpholinyl)propyl]-4-(3,4,5-trimethoxyphenyl)-9-methyl-6H-thieno[3,2-f][1,2,4]triazolo[4,3-a][1,4]diazepine.

The compounds according to the invention have a PAF-antagonistic activity. As is known, PAF (platelet activating factor) is the phospholipid acetyl-glyceryl-ether-phosphoryl-choline (AGEPC), known as a potent lipid mediator which is released by animal or human proinflammatory cells. These cells include, chiefly, basophilic and neutrophilic granulocytes, macrophages (from blood and tissue) and thrombocytes which are involved in reactions of inflammation.

In pharmacological trials, PAF demonstrates bronchoconstriction, lowering of blood pressure, the triggering of thrombocyte aggregation and a proinflammatory activity.

These experimentally demonstrable activities of PAF point directly or indirectly to possible functions of this mediator in anaphylaxis, in the pathophysiology of bronchial asthma and in inflammation in general.

PAF antagonists are needed on the one hand in order to clarify further pathophysiological functions of this mediator in humans and animals and on the other hand to treat pathological conditions and diseases in which PAF is implicated. Examples of indications for a PAF antagonist are inflammatory processes of the tracheobronchial tree (acute and chronic bronchitis, bronchial asthma) or of the kidneys (glomerulonephritis), anaphylactic conditions, allergies and inflammation in the mucous membranes and in the skin (e.g. psoriasis) and shock caused by sepsis, endotoxins or burns. Other important indications for a PAF antagonist include lesions and inflammation in the gastric and intestinal mucous membranes, such as gastritis, and in general peptic ulcers but more particularly ventricular ulcers and duodenal ulcers.

The compounds according to the invention are also suitable for treating the following indications: obstructive lung diseases such as bronchial hyperreactivity, inflammatory diseases of the bronchial passages, such as chronic bronchitis; heart and circulatory diseases such as polytrauma, anaphylaxis, arteriosclerosis, inflammatory intestinal diseases, EPH-gestosis (edema-protein urea hypertension), diseases of the extracorporeal circulation, ischaemic diseases, inflammatory and immunological diseases, immune modulation in transplants of foreign tissue, immune modulation in leukaemia, the propagation of metastasis, e.g. in bronchial neoplasty, diseases of the CNS, such as migraine, agarose phobia (panic disorder), and the compounds according to the invention have also been found to be cyto- and organoprotective, e.g. for neuroprotection, e.g. in cirrhosis of the liver and DIC (disseminated intravascular coaggulation); PAF-associated interaction with tissue hormones (autocoid hormones), lymphokines and other mediators.

PAF-antagonistic activity of individual benzodiazepines is known, see E. Kornecki et al, Science 226, 1454–1456 (1984). Using the method described below, alprazolam was found to have an $IC_{50}$ (concentration for a 50% inhibition of aggregation) of 14 $\mu M$, whilst triazolam was found to have an $IC_{50}$ of 9 $\mu M$. These compounds which have been shown to act as tranquillisers or hypnotics and are commercially available are, however, unsuitable for use as PAF antagonists in therapy in a number of cases owing to their marked sedative effect, in spite of their good PAF-antagonistic activity.

Many of the compounds according to the invention, by contrast, do not have this sedative effect, whilst the PAF-antagonistic activity is substantially better than that of the known benzodiazepines.

The pharmacological test methods used are described hereinafter:

PHARMACOLOGICAL TEST METHODS

The PAF-antagonistic activity of some compounds of formula I was investigated by means of the inhibition of blood platelet aggregation in vitro and the antagonising of the PAF-induced bronchoconstriction in anaesthetised guinea pigs, the lowering of blood pressure in anaesthetised rats and skin wheals in rats. Moreover, these compounds were tested for any possible side effects on the central nervous system.

1. In vitro tests: inhibition of blood platelet aggregation

In order to determine the PAF-antagonistic activity of substances, the PAF-induced aggregation of human thrombocytes in vitro was used. In order to obtain thrombocyte-rich plasma (TRP) blood was taken from an unconstricted vein using a plastic syringe containing 3.8% of sodium citrate solution. The ratio of sodium citrate solution to blood was 1:9. After careful mixing, the citrated blood was centrifuged for 20 minutes at $150 \times g$ (1200 rpm). The thrombocyte aggregation was measured using the method developed by Born and Cross (G. V. R. Born and M. J. Cross, J. Physiol. 168, 178 (1963)), in which PAF is added to the TRP with constant stirring in order to initiate aggregation.

The test substance is added 2 to 3 minutes before aggregation is induced, in a volume of 10 $\mu l$. The solvent used is either distilled water, ethanol and/or dimethylsulphoxide. The controls were given corresponding volumes of this solvent. After the initial absorption had been recorded (2 to 3 minutes) aggregation was induced with PAF ($5 \times 10^{-8}$ M).

The maximum of the first aggregation wave is used to assess the effects of the substance. The PAF-induced maximum absorption rate (=maximum aggregation $\times 100\%$) is simultaneously tested in a parallel mixture (=control mixture in one of the channels of the 2-channel aggregometer) with each test batch (second channel) and is used as the 100% value.

The level of aggregation achieved under the effect of the test substance is given as 100%.

Each test substance is tested at concentrations of from $10^{-3}$ to $10^{-8}$ M with a random sampling range of n=4 in order to investigate an inhibiting effect on the PAF-induced thrombocyte aggregation. A concentration-activity curve is then plotted using 3 concentrations and the $IC_{50}$ is determined (concentration for a 50% inhibition of aggregation). The IC values of compounds of general formula I are generally around levels of less than 9 $\mu M$.

2. In vivo tests 2.1. Antagonisation of the PAF-induced bronchoconstriction in anaesthetised guinea pigs Spontaneously breathing male guinea pigs weighing 300 to 450 g are orally given the test substance for a control carrier 1 hour before the intravenous infusion of PAF (30 ng/(kg$\times$min). The text animals are then anaesthetised by intraperitoneal route with 2 mg/kg of urethane, after which the jugular vein, carotid artery and trachea are cannulated. In the control animals the PAF infusion induces a powerful and long-lasting bronchoconstriction which is measured by means of the volume of breath, compliance and resistance, and also a lowering of blood pressure. After about 7 to 10 minutes the animal dies. With the PAF antagonists described, these effects on breathing and blood pressure and the onset of death can be prevented.

2.2. Antagonisation of the PAF-induced lowering of blood pressure in the anaesthetised rat Male Wistar rats weighing 200 to 250 g with normal blood pressure are anaesthestised by intraperitoneal route with 2 mg/kg of urethane. The carotid artery and jugular vein are cannulated. An intravenous PAF infusion (30 ng/(kg$\times$min)) induces a sharp and long-lasting fall in blood pressure in the control animals. This can be reversed, depending on dosage, by intravenous injections (cumulative administration) of the compounds described. Oral or intravenous administration of the compound before the PAF infusion starts can also prevent the lowering of blood pressure by the above-mentioned PAF infusion, depending on dosage.

2.3. Antagonisation of the PAF-induced skin wheals in the rat (modified according to P. P. Koelzer and K. H. Wehr, Arzneim.-Forsch. 8, 181 (1958)

Intracutaneous injection of PAF induces skin wheals which indicate the PAF-induced increase in the permeability of the blood vessels.

Male Wistar rats with a body weight of 250±20 g are shaved over their abdomens. Then 1 ml/kg of a 1% trypan blue solution is injected through a vein in the animal's tail. Intracutaneous injections of physiological saline solution or PAF solution (12.5 to 15.0 ng per site in 0.1 ml) are administered symmetrically with respect to the centre line (linea alba) at three sites at intervals of about 1.5 cm. Whereas no reaction was observed at the injection site of the saline solution, PAF caused a skin reaction (wheal) which was made visible by blue coloration of varying intensity, depending on the dose of PAF. By simultaneous intracutaneous administration of the compounds described or by intravenous pre-treatment this PAF-induced skin reaction could be prevented.

3. Effects on the central nervous system

It is generally known that substances of this type of structure have central nervous effects which are, however, undesirable for a compound with a PAF-antagonistic activity. Therefore, the compounds described were tested for their hypnogenic and anti-convulsive activities and their effects on locomotion. Possible hypnotic effects were investigated on guinea pigs weighing from 400 to 450 g. Doses of up to 200 mg/kg p.o. of these substances were incapable of causing a hypnotic or sedative effect in these animals.

In order to investigate any anti-convulsive activity it is possible to use pentetrazole antagonism in mice (20 to 25 g body weight) (M. I. Gluckmann, Current Therapeutic Research, 7:721, 1965). In this test, doses of up to 100 mg/kg p.o. of these compounds (administered 1 hour before the pentetrazole) showed no influence on the mortality caused by pentetrazole (125 mg/kg i.p., LD 100). The effect on night motility (locomotion) in mice (body weight 20 to 25 g) can be investigated using a light beam cage. The number of times the light beam is broken is recorded. Doses of up to 300 mg/kg p.o. of the above-mentioned compounds showed no activity.

Table A shows the in vitro results for the inhibition of blood platelets, as described hereinafter.

TABLE A:

| Substance | $IC_{50} \times 10^{-6}$ mol |
|---|---|
| Alprazolam | 14 |
| Triazolam | 9 |
| Example no. | |
| 1 | 0.3 |
| 2 | <0.2 |
| 4 | <0.2 |
| 8 | <0.3 |
| 9 | 0.2 |
| 10 | 1.7 |
| 11 | <0.2 |
| 12 | 0.3 |
| 13 | 0.3 |
| 14i | 0.4 |
| 14l | 0.6 |
| 20 | 0.3 |

TABLE A:-continued

| Substance | $IC_{50} \times 10^{-6}$ mol |
|---|---|
| 23 | 0.9 |
| 25 | 0.9 |
| 27 | 0.2 |
| 45 | 0.3 |
| 49 | 1.0 |
| 50 | 0.6 |
| 54 | 1.1 |
| 56 | 0.3 |
| 58 | <0.2 |
| 60 | 0.9 |
| 64 | <0.2 |
| 71 | 0.9 |
| 75 | 1.9 |
| 98 | 2.3 |
| 104 | 2.2 |

The new compounds of general formula Ia and Ib may be administered to warm-blooded animals topically, orally, parenterally, transdermally or by inhalation. The compounds are present as the active ingredients in conventional pharmaceutical preparations, e.g. in compositions consisting essentially of an inert pharmaceutical carrier and an effect dose of the active substance, such as tablets, both plain and coated, capsules, lozenges, powders, solutions, suspensions, aerosols for inhalation, ointments, emulsions, syrups, suppositories, etc. An effective dosage of the compounds according to the invention is between 1 and 50, preferably between 3 and 20 mg per dose for oral administration, and between 0.01 and 50, preferably between 0.1 and 10 mg per dose for intravenous or intramuscular administration. For inhalation, solutions should be used containing 0.01 to 1.0, preferably 0.1 to 0.5% of active substance.

The Examples which follow serve to illustrate the invention in more detail:

EXAMPLE 1:

2-[4-(2-Chlorophenyl)-9-methyl-6H-thieno[3,2-f][1,2,4]triazolo[4,3-a][1,4]diazepin-2-yl]-ethane-1-sulphonic acid-N'-methylpiperazide 1.1. 3-(1,3-Dioxolan-2-yl)-propane-1-sulphonic acid-N'-methylpiperazide At 0° to 5° C., 87.5 ml of 1.6 molar BuLi solution in hexan (0.14 mol) are added dropwise to 23 g (0.13 mol) of methanesulphonic acid-N'-methylpiperazide dissolved in 200 ml of anhydrous tetrahydrofuran, the resulting suspension is stirred for 90 minutes at ambient temperature and then 23.4 g of 2-(2-bromoethyl)-1,3-dioxolan (0.13 mol) in 200 ml of anhydrous tetrahydrofuran are added dropwise, forming a clear solution. After 5 hours' stirring the solvent is eliminated, the residue is taken up with water/methylene chloride and the aqueous phase is extracted several times with methylene chloride. The methylene chloride solution is dried and the solvent is drawn off. The oil residue is filtered over a column of silica gel using methylene chloride/methanol 9:1 as eluant. After the solvent has been driven off again, 20.7 of the desired compound are obtained as a light coloured oil.

(Yield 57% of theory).

1.2. 3-Formyl-propane-1-sulphonic acid-N'-methylpiperazide 20.7 g (0.074 mol) of 3-(1,3-dioxolan-2-yl)propane-b 1-sulphonic acid-N'-methylpiperazide and 800 ml of 2 N sulphuric acid are stirred for 30 minutes at 80° C., cooled and adjusted to pH 6.5–7 with conc. ammonia. The solution, subsequently saturated with common salt, is thoroughly extracted with methylene chloride. After drying and elimination of the solvent, 13.2 g of the aldehyde are obtained as a light coloured oil.

(Yield 76% of theory).

1.3. 2-Amino-3-(2-chlorobenzoyl)-5-[2-(N'-methyl-piperazinylsulphonyl)ethyl]-thiophene 10.1 g (0.056 mol) of o-chlorocyanoacetophenone and 18 g (0.056 mol) of sulphur are placed in 10 ml of dimethylformamide and 7.8 ml of (0.056 mol) of triethylamine are added dropwise. Then 13.2 g of 3-formyl-n-propane-1-sulphonic acid-N'-methylpiperazide in 50 ml of dimethylformamide are added dropwise and the resulting solution is stirred for 30 minutes at 70° C. After 12 hours the reaction mixture is poured onto 100 ml of ice water and extracted with ethyl acetate. After washing, drying and removal of the solvent, 18 g of oil residue remain which is purified over a silica gel column using methylene chloride/methanol (9:1) as eluant. 15.0 g of the thiophene compound are obtained in the form of a light coloured oil.

(Yield 63% of theory).

$^1$H-NMR (CDCl$_3$) δ ppm 7.30–7.55 (4H, m, aryl-H); 7.14 (2H, s, broad, NH$_2$); 6.18 (1H, s, thiophene-H); 3.18–3.43 (4H, m, piperazine (CH$_2$)$_2$—N); 3.07 (4H, s, SO$_2$CH$_2$CH$_2$); 2.33–2.61 (4H, m, piperazine (CH$_2$)$_2$—N—SO$_2$); 2.33 (3H, s, N—CH$_3$).

1.4. 2-Bromoacetylamino-3-(2-chlorobenzoyl)-5-[2-(N'-methyl-piperazinylsulphonyl)ethyl]thiophene 14 g of the compound of Example 1.3 and 4.6 ml of triethylamine are placed in 200 ml of anhydrous methylene chloride and 2.85 ml of bromoacetylbromide are added dropwise at ambient temperature. After 4 hours, water is added to the reaction mixture which is made slightly alkaline and extracted with methylene chloride. After washing and drying, the solvent is eliminated at a water bath temperature of 30° C. The residues obtained (17.9 g) have to be reacted further immediately.

1.5. 2-Aminoacetylamino-3-(2-chlorobenzoyl)-5-[2-(N'-methylpiperazinylsulphonyl)ethyl]thiophene 17.9 g (0.032 mol) of the compound of Example 1.4 are dissolved in 200 ml of ethyl acetate and ammonia is passed in for 4 hours. The reaction mixture is stirred for 12 hours at ambient temperature, washed several times with water, the organic phase is dried and the solvent is eliminated. 6.1 g of an oily residue are obtained.

(Yield 39% of theory).

1.6. 2-[4-(2-Chlorophenyl)-thieno[3,2-f][1,4]diazepin-7-on-2-yl]-ethane-1-sulphonic acid-N'-methylpiperazide 6.1 g (0.013 mol) of the compound of Example 1.5 and 20 g of silica gel are refluxed for 3 hours with 150 ml of toluene using a water separator. The silica gel is suction filtered with hot methanol. The 5.3 g of crude product obtained after working up are chromatographed on silica gel (eluant: methylene chloride/methanol 9:1). 2.6 g of the diazepinone are obtained (yield 44% of theory), m.p. 135°–138° C. (acetonitrile).

1.7. 2-[4-(2-Chlorophenyl)-thieno[3,2-f][1,4]diazepin-7-thion-2-yl]-ethane-1-sulphonic acid-N'-methylpiperazide 2.6 g (0.0056 mol) of the diazepinone, 1.25 g (0.0028 mol) of phosphorus pentasulphide and 1 g of sodium hydrogen carbonate are stirred for 2 hours in 30 ml of diglyme at 80° C. The reaction mixture is added to 100 ml of water and the solid precipitated is suction filtered. The diazepine thione obtained (yield: 2.7 g, 100% of theory) is reacted further without any purification.

1.8. 2-[4-(2-Chlorophenyl)-9-methyl-6H-thieno[3,2-f][1,2,4]triazolo[4,3-a][1,4]diazepin-2-yl]ethane-1-sulphonic acid-N'-methylpiperazide 2.7 g (0.0056 mol) of the compound of Example 1.7. and 0.3 ml (0.0062 mol) of hydrazine hydrate are stirred for 1 hour at ambient temperature in 30 ml of tetrahydrofuran. After the solvent has been eliminated, the residue is stirred with 10 ml of triethyl orthoacetate for 1 hour at 70° to 80° C. The excess orthoester is then removed, the residue is taken up in 2 N hydrochloric acid and extracted with ether and methylene chloride. The aqueous phase is made alkaline and the thienotriazolodiazepine is extracted with methylene chloride. After evaporation and drying, 1.2 g of crude product are obtained which is chromatographed on aluminum oxide, neutral, activity stage III using methylene chloride/methanol 95:5 as eluant. 1.0 g (yield 35%) of the thienotriazolodiazepine are obtained, m.p. 148°–150° C.

$^1$H-NMR (CDCl$_3$) δ ppm 7.30–7.61 (4H, m, aryl-H); 6.48 (1H, s, thiophene-H); 4.95 (2H, s, 7-ring CH$_2$); 3.00–3.47 (8H, m, piperazine-(CH$_2$)$_2$-N-SO$_2$, SO$_2$—CH$_2$—CH$_2$—); 2.72 (3H, s, triazole-CH$_3$); 2.30–2.61 (4H, m, piperazine-(CH$_2$)$_2$-N); 2.32 (3H, s, piperazine-CH$_3$).

EXAMPLE 2

3-[4-(2-Chlorophenyl)-9-methyl-6H-thieno[3,2-f][1,2,4]triazolo[4,3-a][1,4]diazepin-2-yl]propyl acetate 2.1. 2-Amino-3-(2-chlorobenzoyl)-5-(3-acetoxypropyl)-thiophene Analogously to Example 1, starting from 5-hydroxypentanal, the 2-amino-3-(2-chlorobenzoyl)-5-(3-hydroxy-propyl)-thiophene is synthesised. 1 g (0.0034 mol) of this compound is dissolved in 40 ml of ethyl acetate with gentle heating, after hydrogen chloride has been introduced for 20 minutes the mixture is stirred for a further 2 hours at ambient temperature, the solvent is drawn off, the residue is taken up in methylene chloride and washed with water. After drying and removal of the solvent, the oily residue is chromatographed on silica gel with methylene chloride/methanol 9:1 as eluant. 0.75 g (65% of theory) of the above compound are obtained.

$^1$H-NMR (CDCl$_3$) δ ppm 7.24–7.54 (4H, m, aryl-H); 7.09 (2H, s, broad, NH$_2$); 6.13 (1H, s, thiophene-H); 4.07 (2H, t, J=6 Hz, OCH$_2$); 2.61 (2H, t, J=6 Hz, thiophene-CH$_2$); 2.02 (3H, s, CH$_3$C=O); 1.85 (2H, m, OCH$_2$—CH$_2$—):

2.2. 3-[4-(2-Chlorophenyl)-9-methyl-6H-thieno[3,2-f][1,2,4]triazolo[4,3-a][1,4]diazepin-2-yl]propyl acetate Starting from the compound of Example 2.1., the 2-bromoacetylamino compound is obtained in a 92% yield analogously to Example 1, the 2-aminoacetylamino compound in an 86% yield, the cyclised diazepinone in a 76% yield, the corresponding diazepinethione in a 70% yield and the title compound, m.p. 153°–155° C., in a 76% yield.

EXAMPLE 3

2-(3-Hydroxypropyl)-4-(2-chlorophenyl)-9-methyl-6H-thieno[3,2-f][1,2,4]triazolo[4,3-a][1,4]diazepine (a) Synthesis from the compound of Example 2:

3.0 g (0.0072 mol) of the compound of Example 2 are stirred with one equivalent of potassium hydroxide in 40 ml of ethanol for 12 hours at ambient temperature; the solvent is drawn off in vacuo and the residue is taken up in methylene chloride. After washing, drying and removal of the solvent, 2 g of the title compound are obtained, m.p. 155°-160° C. (yield 74% of theory).

(b) Synthesis from methyl 2-[4-(2-chlorophenyl)-9-methyl-6H-thieno[3,2-f][1,2,4]triazolo[4,3-a][1,4]diazepin-2-yl]-ethane-1-carboxylate 2.5 g (0.0062 mol) of the corresponding methyl ester are dissolved in 25 ml of anhydrous tetrahydrofuran and at ambient temperatures a total of 0.13 g (0.0034 mol) of lithium alanate powder are added in tiny batches. After 12 hours' stirring, with cooling, 0.2 ml of water followed by 0.2 ml of 6 N sodium hydroxide solution and then 0.4 ml of water are added and thoroughly mixed. The solid is suction filtered and the filtrate, after removal of the solvent, is chromatographed on silica gel with methylene chloride/methanol (4:1) as eluant. Traces of the starting compound can be separated off by HPLC column chromatography using methylene chloride/methanol (4:1) as eluant. 1.6 g of compound 3 are obtained (yield 69% of theory).

$^1$H-NMR (CDCl$_3$) δ ppm 7.30-7.52 (4H, m, aryl-H); 6.42 (1H, s, thiophene H); 4.91 (2H, s, 7-ring-CH$_2$); 3.69 (2H, t, J=6 Hz, OCH$_2$); 2.88 (2H, t, J=6 Hz, thiophene-CH$_2$); 2.69 (3H, s, triazole-CH$_3$); 1.91 (2H, m, OCH$_2$C-H$_2$—); 1.78 (1H, s, broad, OH).

The starting compound, methyl 2-[4-(2-chlorophenyl)-9-methyl-6H-thieno[3,2-f][1,2,4]triazolo[4,3-a][1,4]diazepin-2-yl]-ethane-1-carboxylate, is obtained as follows:

2-Amino-3-o-chlorobenzoyl-5-(2-dicarbethoxyethyl)-thiophene 53.9 g (0.3 mol) of o-chlorocyanoacetophenone, 9.6 g of sulphur, 30.4 g (0.3 mol) of triethylamine and 120 ml of dimethylformamide are mixed, with stirring, beginning at ambient temperature, with 64.8 g (0.3 mol) of dicarbethoxybutyraldehyde (D. T. Warner, J. Am. Chem. Soc. 70, 3470 (1948); b.p. 97° C./0.1 mbar), during which time the temperature rises to 45°-50° C. The mixture is stirred for 2 to 3 hours at 60°-70° C., cooled to ambient temperature and 400 ml of water are added. The thiophene derivative formed is extracted three times, each time with 200 ml of methyl-tert.butyketone. After washing with water and drying in organic phase, the mixture is evaporated down and the crystalline residue is recrystallised from isopropanol/water 7:3.

Yield: 90 g (74% of theory), m.p. 96°-98° C.

2-Amino-o-chlorobenzoyl-5-(2-carbomethoxyethyl)thiophene 63 g (0.15 mol) of the above compound are refluxed for 2 hours with 120 ml of ethanol and 32.5 g of caustic potash in 50 ml of water. The mixture is evaporated down in vacuo, diluted with 50 ml of water and acidified with HCl. The greasy acid precipitate is extracted several times with ethyl acetate. The extracts are dried and evaporated down, the residue is refluxed for 2 hours with 300 ml of toluene and 30 ml of dimethylformamide. After the mixture has been evaporated down to about 50 ml, crystals of the monocarboxylic acid are obtained. Yield: 20.5 g. The purified acid melts at 171°-173° C.

The crude acid is stirred for 18 hours at ambient temperature with 400 ml of absolute methanol and 0.4 ml of concentrated sulphuric acid. After the methanol has been evaporated off the remainder is poured onto ice, extracted with methylene chloride and, after further evaporation from isopropylether, 15 g of ester are obtained, m.p. 89°-90° C.

2-Bromoacetylamino-3-o-chlorobenzoyl-5-(2-carbomethoxyethyl)-thiophene 27.8 g (0.09 mol) of the above ester are suspended in 700 ml of toluene and mixed with 10 g of sodium bicarbonate in 57 ml of water. 7.9 ml of bromoacetylbromide are gradually added with stirring at 40°-50° C. and the mixture is stirred for a further 30 minutes. It is washed with water, the toluene phase is dried, concentrated by evaporation in vacuo and crystallised with isopropylether.

Yield: 35-37 g, m.p. 104°-106° C.

2-Aminoacetylamino-3-o-chlorobenzoyl-5-(2-carbomethoxyethyl)-thiophene 35.8 g (0.08 mol) of the above bromoacetyl compound are dissolved in 700 ml of ethyl acetate and dry ammonia is passed in at ambient temperature for 2 to 3 hours with stirring. The mixture is left to stand overnight, washed with ice water, dried, evaporated down, to yield 22 to 25 g of oil amino compound.

7-(2-Carbomethoxyethyl)-5-o-chlorophenyl-thieno-1,4-diazepinone 21.3 g (0.056 mol) of the above compound are dissolved in 500 ml of toluene and refluxed for 2 hours with 75 g of silica gel using a water separator. The SiO$_2$ is removed by suction filtering and the diazepine is extracted with hot methanol. After evaporation of the methanol, 12-15 g of diazepine are obtained, 160° to 162° C.

7-(2-Carbomethoxyethyl)-5-o-chlorophenyl-thieno-1,4-diazepin-2-thione 10 g (0.03 mol) of the above diazepinone are stirred in 100 ml of diglyme with 6.8 g of phosphorus pentasulphide and 5 g of sodium hydrogen carbonate for 3 hours at 70° to 80° C.

The suspension is poured onto ice, stirred for 30 to 45 minutes and the crystals are suction filtered. After drying, 10 g of thione are obtained, m.p. 185° to 186° C.

Methyl 2-[4-(2-chlorophenyl)-9-methyl-6H-thieno[3,2-f][1,2,4]triazolo[4,3-a][1,4]diazepin-2-yl]ethane-1-carboxylate 6.1 g (0.016 mol) of the above sulphur compound are dissolved in 100 ml of tetrahydrofuran and after the addition of 1 g of hydrazine hydrate, stirred for 30 minutes at 45° to 50° C. The mixture is then evaporated down in vacuo. 5 to 5.2 g of oil are left behind, which crystallise with isopropylether (m.p. 175°-177° C.).

On being heated in 35 ml of ortho-acetic acid ester to 80° C., evaporation from methylene chloride ester, the hydrazino compound yields 3 g of the triazolodiazepine, m.p. 114°-115° C.

The same compound can be obtained from the thione with acetic acid hydrazide.

EXAMPLE 4

7-[4-(2-Chlorophenyl)-9-methyl-6H-thieno[3,2-f][1,2,4]triazolo[4,3-a][1,4]diazepin-2-yl]heptyl acetate In accordance with the method described by H. J. Bestmann et al., Chem. Ber. 104, 65 (1971), oleyl acetate is subjected to ozonolysis in methylene chloride at −40° C. and the oxonide formed is reductively cleaved with the equivalent quantity of triphenylphosphine, whilst the triphenylphosphine oxide formed is thoroughly triturated with ether and then precipitated. Traces of unreacted triphenylphosphine may be precipitated in ethereal solution with methyl iodide in the form of the phosphonium salt. The nonanal is conveniently separated from the desired n-acetoxynonanal by separation in a silver mirror column. Starting from 9-acetoxynonanal, analogously to Example 1, the aminothiophene compound, the 2-bromoacetylamino compound and the 2-aminoacetylamino compound are obtained in quantitative yields, diazepinone cyclisation is obtained in a 76% yield, the diazepinethione is obtained in a 65% yield and the 7-[4-(2-chlorophenyl)-9-methyl-6H-thieno[3,2-f][1,2,4]triazolo[4,3-a][1,4]diazepin-2-yl]-heptyl acetate is obtained in the form of an oil in a 33% yield.

$^1$H-NMR (CDCl$_3$) δ ppm 7.26–7.58 (4H, m, aryl-H); 6.36 (1H, s, thiophene-H); 4.92 (2H, s, 7-ring-CH$_2$); 4.06 (2H, t, J=6 Hz, OCH$_2$); 2.76 (2H, t, J=6 Hz, thiophene-CH$_2$); 2.72 (3H, s, triazole-CH$_3$); 2.05 (3H, s, CH$_3$—C=O); 1.15–1.86 (10H, m, OCH$_2$—(CH$_2$)$_5$).

EXAMPLE 5

3-[4-(2-Chlorophenyl)-9-methyl-6H-thieno[3,2-fl-[1,2,4]triazolo[4,3-a][1,4]diazepin-2-yl]propyl)-2-methyl-propionate 0.5 g (0.0013 mol) of 2-(3-hydroxypropyl)-4-(2-chlorophenyl)-9-methyl-6H-thieno[3,2-f][1,2,4]triazolo[4,3-a][1,4]diazepine (Example 3), 0.12 g (0.0015 mol) of pyridine and 0.2 g (0.0013 mol) of isobutyric acid anhydride are stirred for 4 hours at 60° C. After a further 12 hours' stirring at ambient temperature the reaction mixture is combined with 20 ml of water and extracted with ether. After drying and removal of the solvent, the oily residue is chromatographed on silica gel using methylene chloride/methanol (9:1) as eluant and yields the desired title compound in a quantitative yield, m.p. 124°–125° C.

EXAMPLE 6

3-[4-(2-Chlorophenyl)-9-methyl-6H-thieno[3,2-fl-[1,2,4]triazolo[4,3-a][1,4]diazepin-2-yl]-propyl)-methane sulphonate 1.7 g (0.015 mol) of methanesulphonic acid chloride are added to 3.9 g (0.0105 mol) of 2-(3-hydroxypropyl)-4-(2-chlorophenyl)-9-methyl-6H-thieno[3,2-f]-[1,2,4]triazolo[4,3-a][1,4]diazepine (Example 3) in 60 ml of anhydrous methylene chloride and at 10° C. 1.5 g (0.015 mol) of triethylamine are added dropwise. After 12 hours' stirring at ambient temperature the reaction mixture is thoroughly extracted with water, the organic phase is dried, the solvent is removed and the residue is chromatographed on silica gel using methylene chloride/methanol (9:1) as eluant. 3.8 g of the title compound are obtained in a yield of 81% of theory, m.p. 130°–135° C.

EXAMPLE 7

2-(3-Iodopropyl)-4-(2-chlorophenyl)-9-methyl-6H-thieno[3,2-f][1,2,4]triazolo[4,3-a][1,4]diazepine 0.6 g (0.0011 mol) of propyl 3-[4-(2-chlorophenyl)-9methyl-6H-thieno[3,2-f][1,2,4]triazolo[4,3-a][1,4]-diazepin-2-yl]-toluenesulphonate, prepared analogously to Example 6, and a solution of 0.2 g (0.0014 mol) of anhydrous sodium iodide in 15 ml of anhydrous acetone are stirred for 2 hours at ambient temperature. After the solvent has been removed, the residue is taken up in methylene chloride/water, the organic phase is washed several times with water, then dried, the solvent is removed and in this way 0.2 g (yield 36% of theory) of the amorphous title compound are obtained.

$^1$H-NMR (CDCl$_3$) δ ppm 7.30–7.67 (4H, m, aryl-H); 6.44 (1H, s, thiophene-H); 4.94 (2H, s, 7-ring-CH$_2$); 3.20 (2H, t, J=7 Hz), CH$_2$—J); 2.92 (2H, t, J=7 Hz, thiophene-CH$_2$); 2.71 (3H, s, triazole-CH$_3$); 2.12 (2H, m, ICH$_2$CH$_2$—).

EXAMPLE 8

2-(7-N-Phthalimidoheptyl)-4-(2-chlorophenyl)-9-methyl-6H-thieno[3,2-f][1,2,4]triazolo[4,3-a][1,4]-diazepine 3.0 g (0.006 mol) of Heptyl 7-[4-(2-chlorophenyl)-9-methyl-6H-thieno[3,2-f][1,2,4]triazolo[4,3-a][1,4]-diazepin-2-yl]-methanesulphonate and 1.1 g (0.006 mol) of potassium phthalimide are stirred in anhydrous dimethylformamide for 5 hours at 60°–70° C. After cooling, the reaction mixture is poured into 150 ml of ice water, extracted with methylene chloride and, after drying and evaporation, filtered through a small wide silica gel column using methylene chloride/methanol (9:1) as eluant. The phthalimide compound is obtained in quantitative yield in the form of an oil.

$^1$H-NMR (CDCl$_3$) δ ppm 7.62–7.94 (4H, m, phthalaryl-H); 7.26–7.55 (4H, m aryl-H); 6.36 (1H, s, thiophene-H); 4.93 ((2H, s, 7-ring CH$_2$); 3.52 (2H, t, J=6 Hz, N—CH$_2$—); 2.75 (2H, t, J= −6 Hz), thiophene-CH$_2$); 2.69 (3H, s, triazole-CH$_3$); 1.14–1.93 (10H, m, N—CH$_2$—(CH$_2$)$_5$—).

EXAMPLE 9

2-(7-Amino-heptyl)-4-(2-chlorophenyl)-9-methyl-6H-thieno[3,2-f][1,2,4]triazolo[4,3-a][1,4]diazepine 31.7 g (0.057 mol) of the phthalimido compound of Example 8 are dissolved in 300 ml of ethanol and stirred with 13.8 ml of hydrazine hydrate (0.29 mol) for 20 hours at ambient temperature. The solid precipitate is suction filtered and the filtrate is evaporated down and taken up in 2N hydrochloric acid. The unreacted starting compound can be eliminated by extraction with methylene chloride. The aqueous phase is made alkaline and extracted again with methylene chloride. After drying and removal of the solvent, 14.2 g of the amino compound are obtained in the form of an oil (yield: 58% of theory).

$^1$H-NMR CDCl$_3$) δ ppm 7.28–7.63 (4H, m, aryl-H); 6.38 (1H, s, thiophene-H); 4.95 (2H, s, 7-ring-CH$_2$); 2.55–3.10 (6H, m, NCH$_2$, thiophene-CH$_2$, NH$_2$); 2.72 (3H, s, triazole-CH$_3$); 1.07–1.90 (10H, m, N—CH$_2$—(CH$_2$)$_5$—).

EXAMPLE 10

2-(7-Acetylaminoheptyl)-4-(2-chlorophenyl)-9-methyl-6H-thieno[3,2-f][1,2,4]triazolo[4,3-a][1,4]diazepine 0.2 (0.003 mol) of acetyl chloride in 5 ml of anhydrous methylene chloride are added dropwise to 1.3 g (0.003 mol) of the amino compound of Example 9 and 0.4 ml of triethylamine (0.003 mol) in 35 ml of anhydrous methylene chloride and the mixture is stirred for 12 hours at ambient temperature. After washing with water, drying and removal of the solvent, the residue is chromatographed on silica gel with methylene chloride/methanol (95:5) as eluant and 1.1 g of the acetylamino compound are obtained in a yield of 77% of theory in the form of an oil.

¹H-NMR (CDCl₃) δ ppm 7.30-7.58 (4H, m, aryl-H); 6.37 (1H, s, thiophene-H); 5.67 (1H, s, broad, NH); 4.94 (2H, s, 7-ring-CH₂); 3.24 (2H, m, N—CH₂); 2.76 (2H, t, J=6 Hz, thiophene CH₂); 2.72 (3H, s, triazole-CH₃); 1.98 (3H, s, CH₃C=O); 1.21-1.83 (10H, m, N—CH₂(CH₂)₅—).

EXAMPLE 11

2-(3-(N-Morpholinyl)propyl)-4-(2-chlorophenyl)-9-methyl-6H-thieno[3,2-f][1,2,4]triazolo[4,3-a][1,4]-diazepine 2.7 g (0.006 mol) of the compound of Example 6 and 2.6 g (0.030 mol) of morpholine are refluxed for 6 hours in 50 ml of dioxane, then the solvent is eliminated and the residue is taken up in methylene chloride/water. The organic phase is extracted thoroughly with water, then dried and the solvent is removed. The residue is chromatographed on silica gel with methylene chloride/methanol (9:1) as eluant. 1.3 g of morpholine compound are obtained (yield 50% of theory), m.p. 162°-164° C.

By dissolving the substance in methanolic hydrochloric acid and precipitating with ether, the hydrochloride of the title compound is obtained, m.p. 95° C. (decomposition).

EXAMPLE 12

2-(6-Formylhexyl)-4-(2-chlorophenyl)-9-methyl-6H-thieno[3,2-f][1,2,4]triazolo[4,3-a][1,4]diazepine 2.1 g (0.005 mol) of 2-(7-hydroxyheptyl)-4-(2-chlorophenyl)-9-methyl-6H-thieno[3,2-f][1,2,4]triazolo[4,3-a]-[1,4]diazepine (prepared, for example, from the compound of Example 4 by alkaline saponification) dissolved in 5 ml of methylene chloride are added dropwise to 1.5 g (0.0075 mol) of pyridinechlorochromate in 20 ml of methylene chloride, the resulting mixture is stirred for a further 90 minutes at ambient temperature and 50 of ether are added to the solution. The black resinous oil precipitated is thoroughly extracted several times with ether, the ether solutions are combined, suction filtered over Kieselguhr, the filtrate is evaporated down and the residue is chromatrographed on silica gel with methylene chloride/methanol (9:1) as eluant. 0.6 g (yield 29% of theory) of the aldehyde are obtained as a colourless oil.

¹H-NMR (CDCl₃) δ ppm 9.77 (1H, t, J=<2 Hz, CHO); 7.25-7.59 (4H, m, aryl-H); 6.38 (1H, s, thiophene-H); 4.94 (2H, s, 7-ring-CH₂); 2.76 (2H, t, J=6 Hz, thiophene-CH₂); 2.71 (3H, s, triazole-CH₃); 2.41 (2H, m, —CH₂C=O); 1.17-1.90 (8H, m, O=CCH₂(CH₂)₄—).

EXAMPLE 13

2-(3-Acetoxypropyl)-4-(2-chlorophenyl)-9-bromo-6H-thieno[3,2-f][1,2,4]triazolo[4,3-a][1,4]diazepine 4 g (0.010 mol) of 2-(3-acetoxypropyl)-4-(2-chlorophenyl)-6H-thieno[3,2-f][1,2,4]triazole[4,3-a][1,4]diazepine in 60 ml of anhydrous chloroform, 1.9 g (0.012 mol) of bromine and 1.2 g (0.015 mol) of pyridine are stirred for 20 hours at ambient temperature. Then the reaction mixture is thoroughly extracted with water, the organic phase is dried and evaporated down and the residue is purified by chromatography on silica gel using methylene chloride/methanol (9:1) as eluant. 2.3 g of the 9-bromo compound are obtained in a yield of 48% theory in the form of an oil.

¹H-NMR (CDCl₃) δ ppm 7.30-7.62 (4H, m, aryl-H); 6.43 (1H, s, thiophene-H); 4.90 (2H, s, 7-ring-CH₂); 4.11 (2H, t, J=7 Hz, —O—CH₂); 2.89 (2H, t, J=7 Hz, thiophene-CH₂); 2.03 (3H, s, CH₃C=O; 2.00 (2H, m, OCH₂CH₂—).

EXAMPLE 14

2-(3-Hydroxypropyl)-4-(2-chlorophenyl)-9-methyl-6H-thieno[3,2-f]imidazo[1,2-a][1,4]diazepine 6.3 g (0.0114 mol) of propargylamine are added dropwise, at ambient temperature, to 15 g (0.038 mol) of 2-(3-acetoxypropyl)-4-(2-chlorophenyl)-6H-7,8-dihydrothieno[3,2-f][1,4]diazepine-7-thione in 200 ml of anhydrous dioxan, the mixture is stirred for 20 hours and the solvent is removed. The residue is taken up in methylene chloride/water, the organic phase is thoroughly washed with water, dried and concentrated by evaporation. The crude product obtained is triturated with isopropylether, whereupon it crystallises. 13.5 g of 2-(3-acetoxypropyl)-4-(2-chlorophenyl)-6H-7-propargylamino-thieno[3,2-f][1,4]diazepine are obtained (yield 86% of theory), m.p. 122°-124° C.

11 g (0.027 mol) of the intermediate compound thus obtained and 55 ml of concentrated sulfonic acid are heated to 100° C. for 10 minutes in a preheated oil bath, then poured onto ice and adjusted to pH 10 using concentrated ammonia. Extraction with methylene chloride yields 1.2 g of residue which is taken up in 100 ml of methanol and stirred with 0.2 g of potassium hydroxide for one hour at 60° C. After the methanol has been removed, the residue is taken up in methylene chloride/water, the organic phase is thoroughly washed with water, dried, the solvent is removed and the residue is chromatographed on silica gel using methylene chloride/methanol (9:1) as eluant and in this way 0.7 g of the imidazo compound are obtained (yield 7% of theory), m.p. 131°-134° C. ¹H-NMR (CDCl₃) δ ppm 7.22-7.58 (4H, m, aryl-H); 6.89 (1H, q, J<1 Hz, imidazole-H); 6.38 (1H, s, thiophene-H); 4.77 (2H, s, 7-ring-CH₂); 3.68 (2H, t, J=7 Hz, OCH₂); 2.86 (2H, t, J=8 Hz, thiophene-CH₂); 2.42 (3H, d, J=<1 Hz, imidazole, CH₃); 1.88 (2H, m —OCH₂—CH₂—); 2.00 (1H, s, broad, OH).

EXAMPLE 14a 2-(2-Methoxycarbonylethyl)-7-ethoxycarbonyl-6-(2-chlorophenyl)-6H-thieno[3,2-f]imidazo[1,5-a][1,4]-diazepine 9.0 g (0.025 mol) of 7-(2-methoxycarbonylethyl)-5-chlorophenyl)-1,2-dihydro-3H-thieno[2,3-e][1,4]-diazepin-2-one (W. D. Bechtel and K. H. Weber, J. Pharmac. Sci 74, 1265 (1985)), with a melting point of 152°-154° C., are suspended in 25 ml of dimethylformamide and 3.5 g of potassium tert.butoxide are added under nitrogen. The mixture is stirred for 10-15 minutes, cooled to −30° and 4.7 g of diethylchlorophosphate are added within 10-15 minutes.

The mixture prepared from 3.3 g of potassium tert.butoxide and 3.3 g of ethyl isocyanoacetate at −40° in 22 ml of dimethylformamide is added to this solution and the temperature is maintained at −10° C. for 2 hours, after which the reaction mixture is allowed to come up to ambient temperature. 2.5 ml of glacial acetic acid and then 350 ml of water are added, with cooling, and then the reaction mixture is extracted with ethyl acetate. After wasting, drying and evaporating the ethyl acetate phases, the residue is chromatographed over SiO₂. After the addition of ether, 4.0 g of crystals with a melting point of 139°-140° C. are obtained from the eluant.

| $C_{22}H_{20}ClN_3S$ (457.9) | | | | | | | | | |
|---|---|---|---|---|---|---|---|---|---|
| C | 57.7 | H | 4.40 | N | 9.18 | C | 7.74 | S | 7.00 |
|   | 58.0 |   | 4.44 |   | 9.04 |   | 7.55 |   | 6.87 |

EXAMPLE 14b

2-[2-(Morpholin-4-yl-carbonyl)-ethyl]-4-(2-chlorophenyl)-6H-thieno-[3,2-f]imidazo[1,5-a][1,4]diazepine 3.5 g (0.0076 mol) of the diester prepared according to Example 14a are refluxed for one hour in 75 ml of tetrahydrofuran with 0.75 g of NaOH in 75 ml of methanol and 40 ml of water. The mixture is acidified with 2.6 ml of glacial acetic acid and the solution is evaporated down. The crystals of dicarboxylic acid precipitated on the addition of 50 ml of water melt at 275° C. with decomposition. Yield 3.0 g.

This compound was heated together with 100 ml of 1,2,4-trichlorobenzene under nitrogen for one hour. The mixture was filtered and the filtrate was combined with petroleum ether whereupon the 2-(2-carboxyethyl)compound was precipitated. The morpholide, m.p. 158° C., was obtained from this carboxylic acid analogously to Example 3.

| $C_{22}H_{21}ClN_4S$ (440.9) | | | | | | | |
|---|---|---|---|---|---|---|---|
| C | 59.12 | H | 4.80 | N | 12.71 | S | 7.27 |
|   | 60.12 |   | 4.91 |   | 12.54 |   | 7.06 |

EXAMPLE 14c 2-(2-Diethylaminocarbonylethyl)-6-(2-chlorophenyl)-9-methyl-6H-thieno[3,2-f]imidazo[1,2-a][1,4]diazepine Starting from 7-(2-methoxycarbonylethyl)-5-(2-chlorophenyl)-1,2-dihydro-3H-thieno[2,3-e][1,4]diazepin-2-thione (W. D. Bechtel and K. H. Weber, J. Pharm. Sci 74, 1265 (1985)), m.p. 190° C., the corresponding diethylamide, m.p. 201°-203° C. is obtained analogously to the method of synthesis described in Example 14.

EXAMPLE 14d

2-[2-Morpholin-4-yl-carbonyl-ethyl]-6-(2-chlorophenyl)-9-methyl-6H-thieno[3,2-f]imidazo[1,5-a][1,4]diazepine The title compound is obtained from the carboxylic acid described above if morpholine is used instead of diethylamine. M.p. 248°-250° C.

EXAMPLE 14e

2-[1-(Morpholin-4-yl-carbonyl)-prop-1-en-2-yl]-4-(2-chlorophenyl)-9-methyl-6H-thieno[3,2-f][1,2,4]triazolo[4,3,-a][1,4]diazepine (a) 48.8 g (0.2 mol) of 2-acetylamino-3-(2-chlorobenzoyl)thiophene are refluxed for 1½ hours with 500 ml of acetic anhydride and 6 ml of 85% phosphoric acid. The mixture is concentrated by evaporation in vacuo, the residue is mixed with 200 ml of waste and neutralized with 40% sodium hydroxide solution. The crystals are suction filtered and washed with water, methanol and ether. Yield: 49-51 g, m.p. 228°-230° C.

Under nitrogen, 50.3 g of this compound are added to a solution of 10 g of KOH dissolved in 300 ml of methanol and the resulting solution is stirred for 1 to 2 hours at ambient temperature. It is neutralised with 2N hydrochloric acid and the amino derivative is extracted with methylene chloride. After chromatography of the residue, 43 g of 5-acetyl-2-amino-3-(2-chlorobenzoyl)thiophene are obtained, m.p. 190°-191° C.

(b) 5.5 g (0.02 mol) of this compound are taken up in 50 ml of chloroform in order to protect the acetyl group and, after the addition of 2 ml of 1,3-propane dithiol, stirred for 5 minutes at ambient temperature whilst dry HCl gas is passed in. The mixture is then extracted successively with water, dilute sodium hydroxide solution and a gain with water, the organic phase is dried, the solvent is evaporated off and the residue is chromatographed on $SiO_2$ (methylene chloride/ethanol). Using ether, 4.3 g of crystals, m.p. 162°-163° C., are obtained from the residue of the main fraction.

This compound may be reacted analogously to the methods described above (e.g. in Example 3) to obtain the diazepinone (m.p. 260° C.), the diazepinethione (218° C.) and the triazolodiazepine (m.p. 212° C.).

(c) In order to remove the protecting group, 9 g (0.02 mol) of the triazolodiazepine are stirred with 20 g of chloramine T in 200 ml of methanol for 2 hours at ambient temperature. After chromatography on $SiO_2$ (methylene chloride/ethanol 98:2), 3.5-4 g of 2-acetyl-4-(2-chlorophenyl)-9-methyl-6H-thieno[3,2-f][1,2,4]triazolo[4,3-a][1,4]diazepine are obtained.

3.6 g (0.01 mol) of this compound are suspended in 5 ml of benzene and, after the addition of 2.25 g of triethylphosphoroacetate, added dropwise to a prepared solution of 0.23 g of sodium in 5 ml of ethanol. The resulting mixture is sintered for 20 hours at 40° C. and worked up. The ester obtained is saponified with methanolic potassium hydroxide solution. After acidification and working up, 1.4-1.6 g of crystals are obtained, m.p. 296°-28° C.

This carboxylic acid may be converted into the morpholide, m.p. 194°-196° C., analogously to the Examples described above.

EXAMPLE 14f 2 1[2-(Morpholin-4-yl-carbonyl)-pent-4-en-1-yl]-4-(2-chlorophenyl)-9-methyl-6H-thieno[3,2-f][1,2,4]triazolo[4,3-a][1,4]diazepine 20 g (0.05 mol) of 2-amino-3-(2-chlorobenzoyl)-5-(2,2-dicarboethoxyethyl)-thiophene (W. D. Bechtel and K. H. Weber, J. Pharmac. Sci. 74, 1265 (1985)) are suspended in 100 ml of tetrahydrofuran. This suspension is added dropwise to 2.5 g of sodium hydride, suspended in 100 ml of tetrahydrofuran, and stirred for one hour at 30° C. After the addition of 4.5 ml of allylbromide (0.05 mol) the mixture is stirred for two hours at ambient temperature, the reaction mixture is evaporated down, the residue is taken up in methylene chloride and washed with water. From the organic phase, 13 g of crystals are obtained, m.p. 151°-152° C. 13 g (0.03 mol) of this dicarboxylic acid ester are saponified with 30 ml of ethanol, 6 ml of water containing 3.8 g of caustic potash. 11.3 g of dicarboxylic acid are obtained which is decarboxylated by heating for one hour in 20 ml of DMF (120°-130° C.) and yields 6-7 g of monocarboxylic acid, m.p. 202°-203° C.

The methyl ester with can be obtained from this is an oil. This is bromoacetylated, aminated and cyclised to form the diazepinone analogously to the methods described above.

M.p. 162°-165° C.

The diazepinethione which can be obtained from the diazepinone using phosphorus pentasulfide melts at 179° C. and yields the triazolo-thieno-diazepine carboxylic acid, m.p. 207°–208° C. The morpholide is obtained from this via the imidazolide using the method described hereinbefore, in the form of a viscous oil.

EXAMPLE 14g

2[2-Benzyl-2-(morpholin-4-yl-carbonyl)-ethyl]-4-(2-chlorophenyl)-9-methyl-6H-thieno[3,2-f][1,2,4]triazolo-[4,3-a][1,4]diazepine Starting from 2-amino-3-(2-chlorobenzoyl)-5-(2,2-dicarboxyethyl)-thiophene, the title compound is obtained analogously to EXAMPLE 14f by reacting with benzylchloride via the following stages.
Diazepinone m.p. 158°–161° C.
Diazepinethione m.p. 170°–172° C.
Triazolothienodiazepine carboxylic acid m.p. 158°–162° C.

EXAMPLE 14h

2-[2-(N,N-Diethylaminocarbonyl)-n-propyl]-4-(2-chlorophenyl)-9-methyl-6H-thieno[3,2-f][1,2,4]triazolo-[4,3-a][1,4]diazepine 2-Amino-3-(2-chlorobenzoyl)-5-(2,2-dicarboethoxyethyl)thiophene together with methyl iodide yields the corresponding C-methyl compound and also the title compound using the method described above via the following stages:
Diethyldicarboxylate m.p. 181°–182° C.
Monocarboxylic acid m.p. 161°–162° C.
Methyldiazepinonecarboxylate m.p. 179°–180° C.
Methyltriazolothienodiazepine carboxylate in the form of an oil.
Title compound (diethylamide) m.p. 102°–103° C.

EXAMPLE 14i

2-[2-(Morpholin-4-yl-carbonyl)-n-propyl]-4-(2-chlorophenyl)-9-methyl-6H-thieno[3,2-f][1,2,4]triazolo[4,3-a][1,4]diazepine The title compound is obtained analogously to Example 14h using morpholine instead of diethylamine. Oil.

EXAMPLE 14j 2-(2-(N,N-Diethylaminocarbonylethyl)-4-(2-chlorophenyl)-9-methyl-4,5-dihydro-6H-thieno[3,2-f][2,2,4]triazolo-[4,3-a][1,4]diazepine 2.5 g (0.006 mol) of diethylamide (prepared from the carboxylic acid, W. D. Bechtel and K. H. Weber, J. Pharm. Sci 74, 1265 (1985), with diethylamine and dicyclohexylcarbodiimide) are stirred with 2 g of zinc powder, 50 ml of glacial acetic acid and 50 ml of methylene chloride for 15 hours at ambient temperature. Then the mixture is filtered over Kieselguhr, washed with methylene chloride and the filtrate is made alkaline with ammonia. The methylene chloride phase is separated off, washed with water, dried, concentrated by evaporation and the residue is chromatographed over $SiO_2$. 0.8 g of oil are obtained as the main fraction.

EXAMPLE 14k

2-[2-(4,4-Dimethyl-2-oxazolin-2-yl)-ethyl]-4-(2-chlorophenyl)-9-methyl-6H-thieno[3,2-f][1,2,4]triazolo[4,3-a][1,4]diazepine 3 g (7.7 mmol) of 2-[4-(2-chlorophenyl)-9-methyl-6H-thieno[3,2-f][1,2,4]triazolo[4,3-a][1,4]diazepin-2-yl]ethane-1-carboxylic acid, 0.69 g (7.7 mmol) of 2-amino-2-methylpropan-1-ol, 2,35 g (23 mmol) of triethylamine and 4.8 g of carbon tetrachloride are stirred in 15 ml of pyridine/acetonitrile (1:1) at ambient temperature. Within 2 hours a solution of 6.2 g (23.6 mmol) of triphenylphosphine in 15 ml of the above pyridine/acetonitrile mixture is added dropwise to the mixture.

After 15 hours the suspension is evaporated down and the residue is extracted with (1:1) mixtures of ether and ethylacetate. The extracts are evaporated down and the residue remaining is chromatographed on silica gel using dichloromethane/methanol (95:5). The clean fractions are concentrated by evaporation by recrystallising from ether 1.9 g (56%) of the title compound are obtained, m.p. 168° C.

| $C_{22}H_{22}ClN_5OS$ (439.97) | | | | | | | | | |
|---|---|---|---|---|---|---|---|---|---|
| Calculated: | C | 60.05 | H | 5.04 | N | 15.92 | Cl | 8.06 | S | 7.29 |
| Found: | | 59.53 | | 5.08 | | 15.64 | | 8.11 | | 7.17 |

EXAMPLE 14l

2-[3-(N-Morpholinyl)-n-propyl]-4-(2-chlorophenyl)-9-methyl-4,5-dihydro-6H-thieno[3,2-f][1,2,4]triazolo-[4,3-a][1,4]diazepine 1.2 g (0.0027 mol) of 2-[3-(N-Morpholinyl)-n-propyl]-4-(2-chlorophenyl)-9-methyl-6H-thieno[3,2-f][1,2,4]-triazolo[4,3-a][1,4]diazepine in 20 ml of anhydrous THF are added dropwise to a prepared suspension of 0.1 g (0.0027 mol) of lithium aluminium hydride in 20 ml of anhydrous THF at ambient temperature and the mixture is refluxed for one hour. 0.1 ml of water, 0.1 ml of 15% sodium hydroxide solution and 0.3 ml of water are added to the reaction mixture which is then stirred for 30 minutes and the precipitate obtained is suction filtered. The filtrate is concentrated by evaporation, taken up in methylene chloride, washed and dried and the solvent is removed. The residue is chromatographed on silica gel using methylene chloride/methanol 95:5 as eluant. 0.16 g (yield 13%) of the desired compound are obtained, m.p. 135°–138° C.

EXAMPLE 14m

2-[(2-Phenyl-1,3-dioxolan-4-yl)-methyl]-4-(2-chlorophenyl)-9-methyl-6H-thieno[3,2-f][1,2,4]triazolo[4,3-a][1,4]-diazepine 45.7 g (0.4 mol) of 3,4-dihydro-2H-pyran-2-methanol are subjected to ozonolysis in 100 ml of anhydrous methylene chloride at −40°. Then 104.9 g (0.4 mol) of triphenylphosphine in 70 ml of anhydrous methylene chloride are added dropwise and the reaction mixture is slowly brought to ambient temperature over a period of 3 hours. After 12 hours the solvent is removed and the residue is thoroughly digested with ether and the triphenylphosphine oxide precipitated is suction filtered. Any unreacted triphenylphosphine residues are precipitated in ether with methyl iodide in the form of the phosphonium salt and then suction filtered. The solvent is removed from the filtrate and the residue is fractionated in vacuo. 32 g (55% yield) of the 4-formyloxy-5-hydroxypentanal are obtained, $bp_{0.1}=82°–92°$ C. 23 g (0.157 mol) of the aldehyde, 28 g (0.137 mol) of 0-chlorocyanoacetophenone, 5 g (0.157 mol) of sulphur and 16 g (0.157 mol) of triethylamine are used for the thiophene cyclisation in 100 ml of DMF in the usual way and the resulting 2-amino-3-(2-chlorobenzoyl)-5-(2-formyloxy-3-hydroxy-n-propyl)thiophene is refluxed for 2 hours, as the crude product, with 15 g (0.16 mol) of potassium hydroxide in 500 ml of methanol. After removal of the solvent, the residue is taken up in ethyl acetate, washed with water and dried and after the removal of the solvent chromatographed on silica gel with ethyl acetate as eluant. 19.9 g (total yield 39%) of 2-amino-3-(2-chlorobenzoyl)-5-(2,3-dihydroxy-n-propyl)-thiophene are obtained, m.p. 136°-137° C.

5 g (0.016 mol) of the dihydroxythiophene compound, 1.7 g (0.016 mol) of freshly distilled benzaldehyde and a spatula tip of p-toluenesulphonic acid are refluxed in 250 ml of toluene using a water separator. After 2 hours the toluene phase is made alkaline with pyrrolidine, washed with water and dried and the solvent is removed. The residue is chromatographed on silica gel using methylene chloride/methanol (9:1) as eluant and yields 3.8 g (59% yield) of the 1,3-dioxolan compound in the form of a reddish oil (mixture of diastereomers).

The 2-amino-3-(2-chlorobenzoyl)-5-[(2-phenyl-1,3-dioxolan-4-yl)-methyl]thiophene thus obtained is reacted to form the title compound as described in the preceding examples.

EXAMPLE 14n 2-(2-Ethoxycarbonylethyl)-3,9-dimethyl-4-(2-chlorophenyl)-6H-thieno[3,2-f][1,2,4]1-triazolo[4,3-a][1,4]diazepine Starting from 5-(2-chlorophenyl)-6-methyl-7-(2-ethoxycarbonyl-ethyl)1,2-dihydro-3H-thieno[2,3-e][1,4]-diazepin-2-one, the title compound is obtained analogously to the method described in Example 3.

The starting compound is prepared as follows:

11.6 g (0.073 mol) of ethyl 5-oxo-hexanate are reacted with equimolar quantities of o-chloro-2-cyanoacetophenone and sulphur with the addition of 6.7 ml of diethylamine in 30 ml of ethanol for 5 hours at 60° C. according to Gewald. The residue obtained on concentration of the reaction solution is chromatographed on a silica gel column using chloroform as eluant. The resulting aminoketone is converted into the title compound analogously to Example 3. The diazepinone has a melting point of 173°-176° C. (toluene/ether).

| $C_{19}H_{19}ClN_2O_3S$ (390.9) | | | | | | | | | |
|---|---|---|---|---|---|---|---|---|---|
| Calculated: | C | 58.38 | H | 4.90 | Cl | 9.07 | N | 7.17 | S | 8.20 |
| Found: | | 58.08 | | 4.83 | | 8.94 | | 7.11 | | 8.14 |

EXAMPLE 14o

2-[2-(Morpholin-4-yl-carbonyl)-2-(ethoxycarbonyl)ethyl]-4-(2-chlorophenyl)-6H-methyl-6-thieno[3,2-f][1,2,4]triazolo[4,3-a][1,4]diazepine 1 g (0.0021 mol) of 2-[2,2-di(ethoxycarbonyl)-ethyl]-4-(2-chlorophenyl)-9-methyl-6H-thieno[3,2-f][1,2,4]-triazolo[4,3-a][1,4]diazepine and 5 g of morpholine are stirred at 120° C. for 10 hours. The mixture is diluted with 100 ml of water, extracted several times with methylene chloride, the organic phase is washed with water, dried and concentrated by evaporation. The residue thus obtained is chromatographed over a silica gel column (methylene chloride/methanol 97:3). After conventional working up, the title compound is obtained in the form of an amorphous powder.

In the Tables, the following abbreviations are used:
Et=ethyl
Me=methyl
iPr=isopropyl
t-Bu=tert.butyl
Ac=acetyl The following intermediate compounds are prepared analogously to the processes described in the Examples:

TABLE 1

$R_2^*$—(CH$_2$)$_n$— attached to thiophene ring with NH$_2$ and C(=O)R$_3$

| No. | n | R$_3$ | R$_2$* | m.p. |
|---|---|---|---|---|
| 1 | 2 | 2-Cl-phenyl | —SO$_2$—N(morpholino) | oil |
| 2 | 3 | phenyl | —OH | 96–98° C. |
| 3 | 3 | phenyl | —O—C(=O)—CH$_3$ | oil |

TABLE 1-continued

R₂*—(CH₂)n—C(=CH—)—C(S)(NH₂)—... structure with R₃—C(=O)—

| No. | n | R₃ | R₂* | m.p. |
|---|---|---|---|---|
| 4 | 3 | 2-chlorophenyl | —OH | 146–148° C. |
| 5 | 7 | 2-chlorophenyl | —O—C(=O)—CH₃ | oil |
| 5a | 3 | 3,4,5-trimethoxyphenyl (MeO, OMe, OMe) | —OH | oil |
| 5b | 3 | 3,4,5-trimethoxyphenyl (MeO, OMe, OMe) | —OCOCH₃ | oil |
| 5c | 1 | 2-chlorophenyl | —CHOHCH₂OH | 136–137° C. |
| 5d | 1 | 2-chlorophenyl | —CH(O—CH₂)(O—CH(C₆H₅))— (dioxolane with C₆H₅) | oil |
| 5e | 0 | 2-chlorophenyl | —C(=N—O—C(CH₃)₂—CH₂)— (isoxazoline with gem-diCH₃) | 228–230° C. |
| 5f | 1 | " | dioxolane with C(CH₃)₂ | oil |

TABLE 2

Structure: $R_2^*-(CH_2)_n$ attached to thiophene ring with S, substituent NHCOCH$_2$Br, and R$_3$-C(=O)- group.

| No. | n | R$_3$ | R$_2^*$ | m.p. |
|---|---|---|---|---|
| 6 | 2 | 2-Cl-phenyl | $-SO_2-N$(morpholino) | oil |
| 7 | 3 | phenyl (H) | $-O-C(=O)-CH_3$ | oil |
| 8 | 3 | 2-Cl-phenyl | $-O-C(=O)-CH_3$ | oil |
| 9 | 7 | 2-Cl-phenyl | $-O-C(=O)-CH_3$ | oil |
| 9a | 0 | 2-Cl-phenyl | 4,4-dimethyl-oxazolin-2-yl | oil |
| 9b | 1 | 2-Cl-phenyl | $-CH(COOC_2H_5)_2$ | 83–85° C. |
| 9c | 1 | 2-Cl-phenyl | $-CH(O-CH_2-CH(C_6H_5)-O-)$ (dioxolane w/ C$_6$H$_5$) | oil |
| 9d | 1 | 2-Cl-phenyl | $-CH(O-CH_2-C(CH_3)_2-O-)$ (dioxolane w/ gem-diMe) | oil |

TABLE 3

Structure: $R_2^*-(CH_2)_n$ attached to thiophene ring with S, substituent NHCOCH$_2$NH$_2$, and R$_3$-C(=O)- group.

| No. | n | R$_3$ | R$_2^*$ | m.p. |
|---|---|---|---|---|
| 10 | 2 | 2-Cl-phenyl | $-SO_2-N$(morpholino) | 90–92° C. |
| 11 | 3 | phenyl (H) | $-O-C(=O)-CH_3$ | oil |
| 12 | 3 | 2-Cl-phenyl | $-O-C(=O)-CH_3$ | oil |
| 13 | 7 | 2-Cl-phenyl | $-O-C(=O)-CH_3$ | oil |
| 13a | 0 | 2-Cl-phenyl | 4,4-dimethyl-oxazolin-2-yl | oil |
| 13b | 1 | 2-Cl-phenyl | $CH(COOC_2H_5)_2$ | oil |

TABLE 4

Structure: thiophene-fused diazepinone; $R_2^*-(CH_2)_n$ on thiophene; R$_3$ on imine carbon.

| No. | n | R$_3$ | R$_2^*$ | m.p. |
|---|---|---|---|---|
| 14 | 2 | 2-Cl-phenyl | $-SO_2-N$(morpholino) | >200° C. |
| 15 | 3 | phenyl (H) | $-O-C(=O)-CH_3$ | 122–124° C. |

TABLE 4-continued

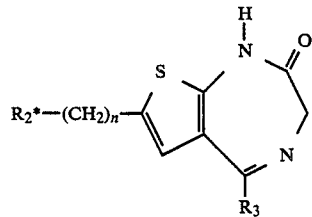

| No. | n | R₃ | R₂* | m.p. |
|---|---|---|---|---|
| 16 | 3 | o-Cl-phenyl | $-O-\underset{\underset{O}{\|\|}}{C}-CH_3$ | 153–155° C. |
| 17 | 7 | o-Cl-phenyl | $-O-\underset{\underset{O}{\|\|}}{C}-CH_3$ | oil |
| 17a | 0 | o-Cl-phenyl | 4,4-dimethyl-oxazolinyl | 242–244° C. |
| 17b | 1 | o-Cl-phenyl | CH(COOC₂H₅)₂ | 144–145° C. |
| 17c | 1 | o-Cl-phenyl | 2,2-dimethyl-1,3-dioxolanyl-methyl | 200° C. |
| 17d | 1 | o-Cl-phenyl | $-\underset{OH}{CH}-\underset{OH}{CH_2}$ | oil |

TABLE 5

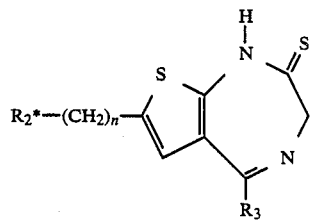

| No. | n | R₃ | R₂* | m.p. |
|---|---|---|---|---|
| 18 | 2 | o-Cl-phenyl | $-SO_2-N\underset{}{\bigcirc}O$ (morpholinyl) | 215–218° C. |
| 19 | 3 | phenyl | $-O-\underset{\underset{O}{\|\|}}{C}-CH_3$ | 170–172° C. |
| 20 | 3 | o-Cl-phenyl | $-O-\underset{\underset{O}{\|\|}}{C}-CH_3$ | 184–185° C. |
| 21 | 7 | o-Cl-phenyl | $-O-\underset{\underset{O}{\|\|}}{C}-CH_3$ | 132–135° C. |
| 21a | 0 | o-Cl-phenyl | 4,4-dimethyl-oxazolinyl | 223–225° C. |
| 21b | 1 | o-Cl-phenyl | -CH(COOC₂H₅)₂ | 158–160° C. |
| 21c | 1 | o-chlorphenyl | $R_2* = -CH\underset{O}{\overset{O}{<}}\underset{CH_3}{\overset{CH_3}{>}}$ | 180° C. |

The compounds of general formula Ia, for example, may be prepared analogously to the examples described hereinbefore:

TABLE 6
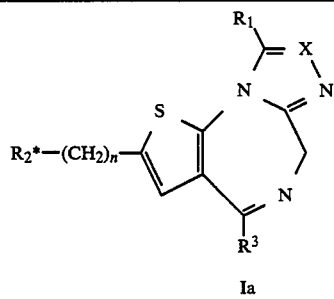
Ia
| No. | R₁ | R₂* | R₃ | X | n | m.p. °C. |
|---|---|---|---|---|---|---|
| 15 | $CH_3$ | OH | 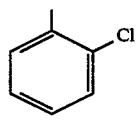 | N | 7 | oil |
| 16 | $CH_3$ | —Cl | " | N | 3 | 142–144 |
| 17 | $CH_3$ | —Cl | " | N | 7 | 84–87 |
| 18 | $CH_3$ | J | " | N | 7 | |
| 19 | $CH_3$ | —$NH_2$ | " | N | 3 | oil |
| 20 | $CH_3$ | 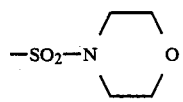 | " | N | 2 | 126–128 |
| 21 | $CH_3$ | —O—$SO_2$—i-Pr | " | N | 3 | |
| 22 | $CH_3$ | 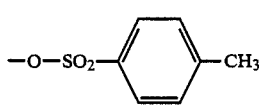 | " | N | 3 | oil |
| 23 | $CH_3$ | —O—$SO_2$—$CH_3$ | " | N | 7 | oil |
| 24 | $CH_3$ | 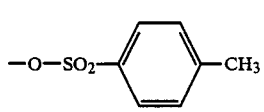 | " | N | 7 | oil |
| 25 | $CH_3$ | —O—CO—t-Bu | " | N | 3 | 163–165 |
| 26 | $CH_3$ | —O—CO—i-Pr | " | N | 7 | oil |
| 27 | $CH_3$ | —CO—t-Bu | " | N | 7 | oil |
| 28 | $CH_3$ | —CO—$NHCH_3$ | " | N | 7 | oil |
| 29 | $CH_3$ | 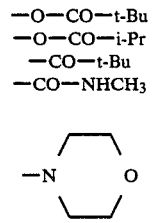 | " | N | 7 | 70–74 (HCl) |
| 30 | $CH_3$ | 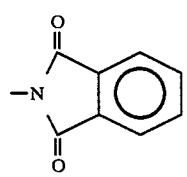 | " | N | 1 | 286–287 |
| 31 | $CH_3$ | 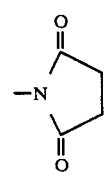 | " | N | 3 | oil |

TABLE 6-continued
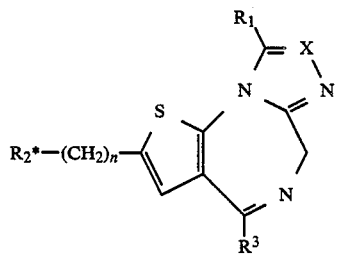
Ia
| No. | R₁ | R₂* | R₃ | X | n | m.p. °C. |
|---|---|---|---|---|---|---|
| 32 | CH₃ | ![phthalimide]  -N(CO)₂C₆H₄ | 2-Cl-C₆H₄ | N | 3 | oil |
| 33 | CH₃ | hydantoin-N- | " | N | 7 | oil |
| 34 | CH₃ | succinimide-N- | " | N | 7 | oil |
| 35 | CH₃ | —NH—CO—CH₃ | " | N | 1 | decomp. |
| 36 | CH₃ | —NH—CO—CH₃ | " | N | 3 | oil |
| 37 | CH₃ | —NH—CO—i-Pr | " | N | 3 | 75–85 |
| 38 | CH₃ | —NH—CO—C₆H₅ | " | N | 3 | 105–115 |
| 39 | CH₃ | —NH—CO—CH₂—N(CH₃)₂ | " | N | 3 | oil |
| 40 | CH₃ | —NH—SO₂—C₆H₄—NH—CO—CH₃ | " | N | 3 | 148–155 |
| 41 | CH₃ | —NH—CO—i-Pr | " | N | 7 | oil |
| 42 | CH₃ | —NH—CO—C₆H₅ | " | N | 7 | 105/decomp. |
| 43 | CH₃ | —NH—CO—CH₂—N(CH₃)₂ | " | N | 7 | oil |

TABLE 6-continued structure Ia:

R₁—C(=X—N)... fused thieno-triazolo-diazepine with R₂*—(CH₂)ₙ— on thiophene and R₃ on the C=N

| No. | R₁ | R₂* | R₃ | X | n | m.p. °C. |
|---|---|---|---|---|---|---|
| 44 | $CH_3$ | —NH—SO₂—C₆H₄—NH—CO—CH₃ (para) | 2-Cl-C₆H₄ | N | 7 | 135/Z. |
| 45 | $CH_3$ | piperidin-1-yl | " | N | 3 | oil |
| 46 | $CH_3$ | 2,6-dimethylmorpholin-4-yl | " | N | 3 | 86–90 |
| 47 | $CH_3$ | " | " | N | 7 | oil |
| 48 | $CH_3$ | 4-methylpiperazin-1-yl | " | N | 3 | oil |
| 49 | $CH_3$ | 4-methylpiperazin-1-yl | " | N | 7 | oil |
| 50 | H | —O—CO—CH₃ | " | N | 3 | 97–98 |
| 51 | $CH_3$ | —O—CO—CH₃ | C₆H₅ | N | 3 | 143–145 |
| 52 | $CH_3$ | —OH | " | N | 3 | 160–163 |
| 53 | $CH_3$ | —O—SO₂—CH₃ | " | N | 3 | 76–79 |
| 54 | $CH_3$ | morpholin-4-yl | " | N | 3 | oil |
| 55 | $OCH_3$ | —O—CO—CH₃ | 2-Cl-C₆H₄ | N | 3 | |
| 56 | $CH_3$ | —O—CO—CH₃ | " | CH | 3 | oil |

TABLE 6-continued
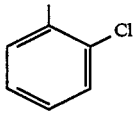
| No. | R₁ | R₂* | R₃ | X | n | m.p. °C. |
|---|---|---|---|---|---|---|
| 57 | CH₃ | —OH | 2-Cl-phenyl | CH | 7 | |
| 58 | CH₃ | —O—CO—CH₃ | " | CH | 7 | oil |
| 59 | CH₃ | —N(CH₃)₂ | " | N | 7 | 92–95° C. (HCl) |
| 60 | CH₃ | —NH(CH₂)₂N(CH₃)₂ | " | N | 7 | 55–60° C. (HCl) |
| 61 | CH₃ | —N-imidazolyl | " | N | 7 | 80–83° C. (HCl) |
| 62 | CH₃ | —N-1,2,4-triazolyl | " | N | 7 | 85–87° C. (HCl) |
| 63 | CH₃ | —N-imidazolyl | " | N | 3 | 56–60° C. |
| 64 | CH₃ | —N-1,2,4-triazolyl | " | N | 3 | 61–65° C. |
| 65 | CH₃ | —N(CH₃)₂ | " | N | 3 | oil |
| 66 | CH₃ | —NH(CH₂)₂N(CH₃)₂ | " | N | 3 | 60–65° C. |
| 67 | CH₃ | —NH—SO₂—C₆H₄—NH₂ | 2-Cl-phenyl | N | 3 | |
| 68 | CH₃ | —NH—SO₂—C₆H₄—NH₂ | " | N | 7 | |
| 69 | CH₃ | —N-piperidinyl | " | N | 7 | oil |
| 70 | OCH₃ | —OH | " | N | 3 | |
| 71 | CH₃ | N(C₂H₅)₂ | " | N | 3 | oil |

TABLE 6-continued
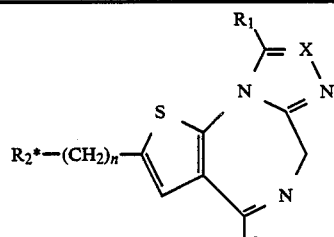
Ia
| No. | R₁ | R₂* | R₃ | X | n | m.p. °C. |
|---|---|---|---|---|---|---|
| 72 | $CH_3$ | pyrazol-1-yl | " | N | 3 | oil |
| 73 | $CH_3$ | pyrazol-1-yl | " | N | 7 | oil |
| 74 | $CH_3$ | pyrrol-1-yl | " | N | 7 | oil |
| 75 | $CH_3$ | $-NH(CH_2)_2-$morpholino | " | N | 3 | 241 |
| 76 | $CH_3$ | $-NHCH_2-$furyl | " | N | 7 | 70-73 |
| 77 | $CH_3$ | $-NH(CH_2)_2-$indol-3-yl | " | N | 7 | amorphous |
| 78 | $CH_3$ | 4,4-dimethyl-oxazolin-2-yl-methyl | " | N | 0 | 174-176 |
| 79 | $CH_3$ | $-CH(CO_2C_2H_5)_2$ | 2-chlorophenyl | N | 1 | 112-114 |
| 80 | $CH_3$ | 2-phenyl-1,3-dioxolan-4-yl | " | N | 1 | |
| 81 | $CH_3$ | 2,2-dimethyl-1,3-dioxolan-4-yl | " | N | 1 | oil |
| 82 | $CH_3$ | $-CH(OH)-CH_2OH$ | " | N | 1 | oil |

TABLE 6-continued

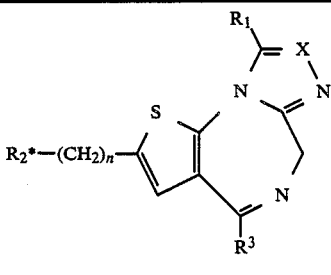

Ia

| No. | R₁ | R₂* | R₃ | X | n | m.p. °C. |
|-----|----|----|----|---|---|----------|
| 83 | CH₃ | —CH—CH₂ with OAc, OAc | " | N | 1 | |
| 83a | CH₃ | C₆H₅—CH₂—CH— with morpholine-N—CH₂ | 2-Cl-C₆H₄ | N | 1 | 134–138° |
| 83b | CH₃ | C₆H₅—CH₂—CH— / CH₃—SO₂—O—CH₂ | " | N | 1 | oil |
| 83c | CH₃ | C₆H₅—CH₂—CH— / HO—CH₂ | " | N | 1 | 148–150° |
| 83d | CH₃ | —OC₆H₅ | " | N | 3 | oil |
| 83e | CH₃ | —OCH₃ | " | N | 3 | oil |
| 83f | CH₃ | —NH—(CH₂)₂-indol-3-yl | " | N | 3 | oil |
| 83g | CH₃ | —OAc | 3,4,5-trimethoxyphenyl (MeO, OMe, OMe) | N | 3 | oil |
| 84 | CH₃ | CH₃SO₂O—CH—CH₂—OSO₂CH₃ | 2-Cl-C₆H₄ | N | 1 | |
| 85 | CH₃ | —CH—CH₂ bis(morpholino) bridged | " | N | 1 | |
| 86 | CH₃ | —CH—CH₂ bis(2,6-dimethylmorpholino) | " | N | 1 | |

TABLE 6-continued

[Structure Ia: thieno-triazolo-diazepine core with R1, R2*-(CH2)n, R3, X substituents]

| No. | R₁ | R₂* | R₃ | X | n | m.p. °C. |
|-----|-----|-----|-----|---|---|----------|
| 87 | CH₃ | −CH(NEt₂)−CH₂(NEt₂) | " | N | 1 | |
| 88 | CH₃ | −CH(N(Me)(iPr))−CH₂(N(Me)(iPr)) | " | N | 1 | |
| 89 | CH₃ | −CH(N-phthalimido)−CH₂(N-phthalimido) | " | N | 1 | |
| 90 | CH₃ | −CH(NH₂)−CH₂(NH₂) | 2-Cl-C₆H₄ | N | 1 | |
| 91 | CH₃ | −CH(NHAc)−CH₂(NHAc) | " | N | 1 | |
| 92 | CH₃ | −CH(OAc)−CH₂(N-morpholino) | " | N | 1 | |
| 93 | CH₃ | −CH(OH)−CH₂(N-morpholino) | " | N | 1 | |
| 94 | CH₃ | −CH(N-morpholino)−CH₂(OAc) | " | N | 1 | |
| 95 | CH₃ | −CH(N-morpholino)−CH₂(OH) | " | N | 1 | |

TABLE 6-continued

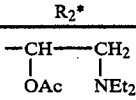

Ia

| No. | $R_1$ | $R_2*$ | $R_3$ | X | n | m.p. °C. |
|---|---|---|---|---|---|---|
| 96 | $CH_3$ | —CH—CH$_2$<br>      \|       \|<br>     OAc  NEt$_2$ | " | N | 1 | |
| 97 | $CH_3$ | —CH—CH$_2$<br>      \|       \|<br>     OH   NEt$_2$ | " | N | 1 | |

TABLE 8

| | | | Compounds db | | | | | |
|---|---|---|---|---|---|---|---|---|
| No. | $R_1$ | $R_2$ | Zn | $R_3$ | R° | R' | X Y | m.p. |
| 98 | $CH_3$ | —OH | —(CH$_2$)$_3$— | 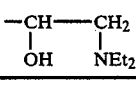 | H | H | N N | oil |
| 99 | $CH_3$ | —OAc | —(CH$_2$)$_3$— | 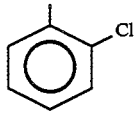 | H | H | N N | oil |
| 100 | $CH_3$ | —OAc | —(CH$_2$)$_3$— | 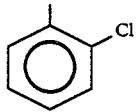 | —Ac | H | N N | oil |
| 101 | $CH_3$ | OH | —CH$_2$—HC—(CH$_2$)—<br>            \|<br>           CH$_2$—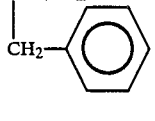 | 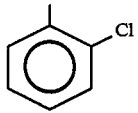 | —Ac | H | N N | 148–150° C. |
| 102 | $CH_3$ | O—SO$_2$CH$_3$ | —CH$_2$—HC—(CH$_2$)—<br>            \|<br>           CH$_2$—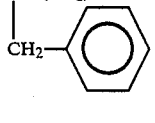 | 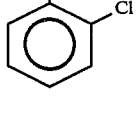 | —Ac | H | N N | |
| 103 | $CH_3$ | 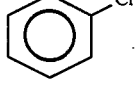 | —CH$_2$—HC—(CH$_2$)—<br>            \|<br>           CH$_2$—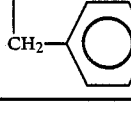 | 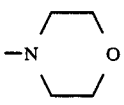 | —Ac | H | N N | |

The following are examples of pharmaceutical compositions using compounds of general formula I as active ingredient. Unless otherwise stated, the parts given are parts by weight.

1. Tablets

A tablet contains the following ingredients:

| | |
|---|---|
| Active substance according to Formula Ia/b | 0.020 parts |
| Stearic acid | 0.010 parts |
| Dextrose | 1.890 parts |
| Total | 1.920 parts |

Preparation:

The substances are mixed together in known manner and the mixture is compressed to form tablets, each weighing 1.92 g and containing 20 mg of active substance.

2. Ointment

The ointment consists of the following ingredients:

| Active substance according to Formula Ia/b | 50 mg |
|---|---|
| Neribas ointment (brand name Scherax) | ad 10 g |

Preparation:

The active substance is triturated with 0.5 g of ointment base and the remaining base is gradually mixed in, in batches of 1.0 g, to form an ointment. A 0.5% ointment is obtained. The distribution of the active substance in the base is optically monitored under a microscope.

3. Cream

Composition:

| Active substance of Formula Ia/b | 50 mg |
|---|---|
| Neribas ointment (Brand name Scherax) | ad 10 g |

Preparation

The active substance is triturated with 0.5 g of the cream base and the remaining base is gradually incorporated in amounts of 1.0 g using a pestle. A 0.5% cream is obtained. The distribution of the active substance in the base is optically monitored under the microscope.

4. Ampoule solution

| Composition: | | |
|---|---|---|
| Active substance of Formula Ia/b | | 1.0 mg |
| Sodium chloride | | 45.0 mg |
| Water for injections | ad | 5.0 ml |

Preparation

The active substance is dissolved in water at its own pH, optionally at pH5 to 7, and sodium chloride is added to make the solution isotonic. The solution obtained is filtered to remove any pyrogens and the filtrate is transferred under aseptic conditions into ampoules which are then sterilised and sealed by fusion. The ampoules contail 1 mg, 5 mg and 1 mg of active substance.

5. Suppositories

Each suppository contains:

| Active substance of Formula Ia/b | 1.0 parts |
|---|---|
| Cocoa butter (m.p. 36–37° C.) | 1200.0 parts |
| Carnauba wax | 5.0 parts |

Preparation

The cocoa butter and carnauba wax are melted together. At 45° C. the active substance is added and the mixture is stirred until complete dispersion is obtained. The mixture is poured into suitably sized moulds and the suppositories are suitably packaged.

6. Solutions for inhalation

Composition:

| (a) Active substance of | | 500 mg |
|---|---|---|
| Formula Ia/b | | |
| Na-EDTA | | 50 mg |
| Benzylconium chloride | | 25 mg |
| Sodium chloride | | 880 mg |
| Distilled water | ad | 100 ml |

Preparation:

96% of the quantity of water is put in, then the Na-EDTA, benzylconium chloride, sodium chloride and active substance are successively dissolved therein until clear and the remaining water is added. The solution is transferred into 20 ml dropper vials. One dose (20 drops, 1 ml) contains 5 mg of active substance.

| (b) Active substance of | | 500 mg |
|---|---|---|
| Formula Ia/b | | 500 mg |
| Sodium chloride | | 820 mg |
| Distilled water | ad | 100 ml |

Preparation

96% of the quantity of water is put in, then the active substance and sodium chloride are successively dissolved therein, the remaining water is added and the solution is transferred into single dose containers (4 ml). The solution contains 20 mg of active substance.

Table 9 gives the NMR spectra of selected compounds of general formula Ia and Ib.

Table 9

EXAMPLE 15

$^1$H-NMR (CDCl$_3$) $\delta$ ppm 7.23–7.62 (4H, m, aryl-H); 6.36 (1H, s, thiophene-H); 4.92 (2H, s, CH$_2$-7-ring); 3.62 (2H, t, J=6 Hz, OCH$_2$); 2.77 (2H, t, J=6 Hz, CH$_2$-thiophene); 2.72 (3H, s, triazole-CH$_3$), 2.07 1H, s, broad, OH); 1.17–1.89 (10H, m, OCH$_2$—(CH$_2$)$_5$—).

EXAMPLE 19

$^1$-NMR (CDCl$_3$) $\delta$ ppm 7.22–7.57 (4H, m, aryl-H); 6.44 (1H, s, thiophene-H); 4.95 (2H, s, 7-ring-CH$_2$); 2.85 (2H, t, J=6 Hz, thiophene-CH$_2$); 2.80 (2H, t, J=6 Hz, NCH$_2$); 2.71 (3H, s, triazole-CH$_3$), 2.44 (2H, s, broad, NH$_2$); 1.84 (2H, m, NCH$_2$—CH$_2$—).

EXAMPLE 22

$^1$H-NMR (CDCl$_3$) $\delta$ ppm 7.22–7.87 (8H, m, aryl-H); 6.40 (1H, s, thiophene-H); 4.92 (2H, s, 7-ring-CH$_2$); 4.06 (2H, t, J=6 Hz, OCH$_2$); 2.87 (2H, t, J=6 Hz, thiophene-CH$_2$); 2.67 (3H, s, triazole-CH$_3$), 2.44 (3H, s, Aryl-CH$_3$); 2.01 (2H, m, —OCH$_2$CH$_2$—).

EXAMPLE 23

$^1$NMR (CDCl$_3$) $\delta$ ppm 7.23–7.58 (4H, m, aryl-H); 6.37 (1H, s, thiophene-H); 4.93 (2H, s, 7-ring-CH$_2$); 4.21 (2H, t, J=7 Hz, OCH$_2$); 2.99 (3H, s, CH$_3$SO$_2$); 2.75 (2H, t, J=7 Hz, thiophene-CH$_2$); 2.70 (3H, s, triazole-CH$_3$); 1.14–1.98 (10H, m, OCH$_2$—(CH$_2$)$_5$).

EXAMPLE 24

$^1$H-NMR (CDCl$_3$) $\delta$ ppm 7.22–7.84 (8H, m, aryl-H); 6.36 (1H, s, thiophene-H); 4.93 (2H, s, 7-ring-CH$_2$); 4.01 (2H, t, J=6 Hz, OCH$_2$) 2.81 (2H, m, thiophene-CH$_2$); 2.71 (3H, s, triazole-CH$_3$); 2.49 (3H, s, aryl-CH$_3$); 1.16–1.89 (10H, m, OCH$_2$—(CH$_2$)$_5$).

EXAMPLE 26

$^1$H-NMR (CDCl$_3$) δ ppm 7.30–7.59 (4H, m, aryl-H); 6.37 (1H, s, thiophene-H); 4.95 (2H, s, 7-ring-CH$_2$); 4.06 (2H, t, J=6 Hz, OCH$_2$—); 2.77 (2H, t, J=6 Hz, thiophene-CH$_2$); 2.72 (3H, s, triazole-CH$_3$); 2.53 (1H, m, CH—C=O); 1.26–1.89 (10H, m, OCH$_2$—(CH$_2$)$_5$—); 1.28 (6H, d, J=5 Hz, (CH$_3$)$_2$—CH—).

EXAMPLE 27

$^1$H-NMR (CDCl$_3$) δ ppm 7.31–7.58 (4H, m, aryl-H); 6.37 (1H, s, thiophene-H); 4.94 (2H, s, 7-ring-CH$_2$); 4.04 (2H, t, J=6 Hz, OCH$_2$); 2.71 (3H, s, triazole-CH$_3$); 2.77 (2H, t, J=7 Hz, thiophene-CH$_2$); 1.23–1.93 (10H, m, OCH$_2$(CH$_2$)$_5$—); 1.20 (9H, s, C(CH$_3$)$_3$).

EXAMPLE 28

$^1$H-NMR (CDCl$_3$) δ ppm 7.31–7.59 (4H, m, aryl-H); 6.37 (1H, s, thiophene-H); 4.94 (2H, s, 7-ring-CH$_2$); 4.69 (1H, s, broad, NH); 4.04 (2H, t, J=7 Hz, OCH$_2$); 2.78 (3H, d, J=6 Hz, CH$_3$N); 2.76 (2H, t, J=7 Hz, thiophene-CH$_2$); 2.71 (3H, s, triazole-CH$_3$); 1.20–1.85 (10H, m, OCH$_2$—(CH$_2$)$_5$—).

EXAMPLE 31

$^1$H-NMR (CDCl$_3$) δ ppm 7.30–7.61 (4H, m, aryl-H); 6.44 (1H, s, thiophene-H); 4.94 (2H, s, 7-ring-CH$_2$); 3.59 (2H, t, J=7 Hz, N—CH$_2$); 2.81 (2H, t, J=7 Hz, thiophene-CH$_2$); 2.71 (7H, s, succine-CH$_2$CH$_2$-, triazole-CH$_3$); 1.93 (2H, m, N—CH$_2$CH$_2$).

EXAMPLE 32

$^1$H-NMR (CDCl$_3$) δ ppm 7.62–7.95 (4H, m, phthalidearyl-H); 7.28–7.56 (4H, m, aryl-H); 6.43 (1H, s, thiophene-H); 4.87 (2H, s, 7-ring-CH$_2$), 3.76 (2H, t, J=6 Hz, N—CH$_2$); 2.86 (2H, t, J=6 Hz, thiophene-CH$_2$), 2.70 (3H, s, triazole-CH$_3$); 2.06 (2H, m, N—CH$_2$CH$_2$—).

EXAMPLE 33

$^1$H-NMR (CDCl$_3$) δ ppm 7.28–7.58 (4H, m, aryl-H); 6.35 (1H, s, broad, NH); 6.35 (1H, s, thiophene-H); 4.93 (2H, s, 7-ring-CH$_2$); 3.92 (2H, s, imidazolidione-CH$_2$); 3.46 (2H, t, J=7 Hz, N—CH$_2$); 2.75 (2H, t, J=7 Hz, thiophene-CH$_2$); 2.71 (3H, s, triazole-CH$_3$); 1.13–1.86 (10H, m, N—CH$_2$—(CH$_2$)$_5$).

EXAMPLE 34

$^1$H-NMR (CDCl$_3$) δ ppm 7.30–7.51 (4H, m, aryl-H); 6.44 (1H, s, thiophene-H); 4.98 (2H, s, 7-ring-CH$_2$); 3.51 (2H, t, J=6 Hz, N—CH$_2$); 2.76 (2H, t, J=6 Hz, thiophene-CH$_2$); 2.74 (3H, s, triazole-CH$_3$); 2.71 (4H, s, succine-CH$_2$); 1.23–1.74 (10H, m, N—CH$_2$—(CH$_2$)$_5$—).

EXAMPLE 35

$^1$H-NMR (CDCl$_3$) δ ppm 7.21–7.52 (4H, m, aryl-H); 7.27 (1H, t, J=6 Hz, NH); 6.54 (1H, s, thiophene-H); 4.84 (2H, s, 7-ring-CH$_2$); 4.47 (2H, d, J=6 Hz, N—CH$_2$); 2.6 (3H, s, triazole-CH$_3$); 2.00 (3H, s, CH$_3$—C=O).

EXAMPLE 36

$^1$H-NMR (CDCl$_3$) δ ppm 7.33–7.57 (4H, m, aryl-H); 6.54 (1H, t, J=6 Hz, NH); 6.46 (1H, s, thiophene-H); 4.96 (2H, s, 7-ring-CH$_2$); 3.32 (2H, q, J=6 Hz, NH—CH$_2$); 2.83 (2H, t, J=6 Hz, thiophene-CH$_2$); 2.71 (3H, s, triazole-CH$_3$); 1.98 (3H, s, CH$_3$—CO); 1.88 (2H, m, N—CH$_2$—CH$_2$—).

EXAMPLE 39

$^1$H-NMR (CDCl$_3$) δ ppm 7.03–7.62 (5H, m, aryl-H and NH); 6.40 (1H, s, thiophene-H); 4.93 (2H, s, 7-ring-CH$_2$); 3.33 (2H, q, J=6.5 Hz, CH$_2$-NH); 2.94 (2H, s, CH$_2$C=O); 2.82 (m, CH$_2$-thiophene); 2.70 (3H, s, triazole-CH$_3$); 2.27 (6H, s, N—(CH$_3$)$_2$); 1.89 (2H, m, N—CH$_2$—CH$_2$—).

EXAMPLE 41

$^1$H-NMR (CDCl$_3$) δ ppm 7.25–7.60 (4H, m, aryl-H); 6.37 (1H, s, thiophene-H); 5.64 (1H, s, broad, NH); 4.94 (2H, s, 7-ring-CH$_2$); 3.23 (2H, m, N—CH$_2$); 2.76 (2H, t, J=6 Hz, thiophene-CH$_2$); 2.71 (3H, s, triazole-CH$_3$); 2.33 1H, m, CH—C=O); 1.21–1.87 (10H, m, N—CH$_2$—(CH$_2$)$_5$); 1.16 (6H, d, J=8 Hz, (CH$_3$)$_2$—C).

EXAMPLE 43

$^1$H-NMR (CDCl$_3$) δ ppm 7.45–7.60 (4H, m, aryl-H); 7.17 (1H, s, broad, NH); 6.34 (1H, s, thiophene-H); 4.93 (2H, s, 7-ring CH$_2$); 3.27 (2H, q, J=6.5 Hz, CH$_2$NH); 2.94 (2H, s, CH$_2$C=O); 2.71 (3H, s, triazole-CH$_3$); 2.71 (2H, m, CH$_2$-thiophene); 2.28 (6H, s, N(CH$_3$)$_2$); 1.21–1.88 (10H, m, (CH$_2$)$_5$).

EXAMPLE 45

$^1$H-NMR (CDCl$_3$) δ ppm 7.24–7.58 (4H, m, aryl-H); 6.38 (1H, s, thiophene-H); 4.93 (2H, s, 7-ring-CH$_2$); 2.79 (2H, t, J=8 Hz, N—CH$_2$); 2.69 (3H, s, triazole-CH$_3$); 1.24–2.49 (14H, m, piperidine-CH$_2$, thiophene-CH$_2$—CH$_2$).

EXAMPLE 47

$^1$H-NMR (CDCl$_3$) δ ppm 7.19–7.59 (4H, m, aryl-H); 6.36 (1H, s, thiophene-H); 4.93 (2H, s, 7-rings-CH$_2$); 3.68 (2H, m, 2,6-morpholine-CH-); 2.71 (3H, s, triazole-CH$_3$); 1.16, 1.23 (6H, 2d, J=6 Hz, 2,6-morpholine-CH$_3$); 1.01–2.91 (18H, m, morpholine-NCH$_2$/N—(CH$_2$)$_7$)

EXAMPLE 48

$^1$H-NMR (CDCl$_3$) δ ppm 7.24–7.56 (4H, m, aryl-H); 6.38 (1H, s, thiophene-H); 4.92 (2H, s, 7-ring-CH$_2$); 2.80 (2H, t, J=7 Hz, N—CH$_2$); 2.70 (3H, s, triazole-CH$_3$); 2.42 (8H, s, piperazine-CH$_2$); 2.37 (2H, t, J=7 Hz, thiophene-CH$_2$); 2.27 (3H, s, N—CH$_3$), 1.86 (2H, m, N—CH$_2$—CH$_2$).

EXAMPLE 49

$^1$H-NMR (CDCl$_3$) δ ppm 7.24–7.59 (4H, m, aryl-H); 6.36 (1H, s, thiophene-H); 4.93 (2H, s, 7-ring-CH$_2$); 2.74 (2H, t, J=7 Hz), N—CH$_2$); 2.71 (3H, s, triazole-CH$_3$); 2.44 (8H, s, piperazine-CH$_2$); 2.28 (2H, t, J=7 Hz, thiophene-CH$_2$); 2.27 (3H, s, N—CH$_3$); 1.08–1.88 (10H, m, N—CH$_2$—(CH$_2$)$_5$).

EXAMPLE 54

$^1$H-NMR (CDCl$_3$) δ ppm 7.20–7.73 (5H, m, aryl-H); 6.64 (1H, s, thiophene-H); 4.87 (2H, s, 7-ring-CH$_2$); 3.71 (4H, m, morpholine-OCH$_2$); 2.89 (2H, t, J=7 Hz, N—CH$_2$); 2.69 (3H, s, triazole-CH$_3$); 2.21–2.57 (6H, m, morpholine-N-CH$_2$/thiophene-CH$_2$); 1.90 (2H, m, N—CH$_2$—CH$_2$—).

EXAMPLE 56

$^1$H-NMR (CDCl$_3$): δ 7.21–7.62 (m, 4H, aryl-H); 6.92 (qu, J<1 Hz, CH=); 6.41 (s, 1H, thiophene-H); 4.81 (s, 2H, CH$_2$-7-ring); 4.12 (t, J=7 Hz, 2H, OCH$_2$); 2.86 (t, J=7 Hz, 2H, CH$_2$-thiophene); 2.45 (d, J<1 Hz, 3H, CH$_3$-imidazole); 2.05 (s, 3H, CH$_3$—C=O); 2.00 (m, 2H, OCH$_2$CH$_2$).

EXAMPLE 58

$^1$H-NMR (CDCl$_3$); δ 7.21–7.60 (m, 4H, aryl-H); 6.91 (qu, J<1 Hz, 1H, CH=); 6.35 (s, 1 H, thiophene-H); 4.79 (s, 2H, CH$_2$-7-ring); 4.06 (t, J=7 Hz, 2H, OCH$_2$); 2.76 (t, J=7 Hz, 2H, CH$_2$-thiophene); 2.46 (d, J=<1 Hz, 3H, CH$_3$-imidazole); 2.05 (s, 3H, CH$_3$C=O); 1.15–1.91 (m, 10H, OCH$_2$—(CH$_2$)$_5$—).

EXAMPLE 65

$^1$H-NMR (CDCl$_3$): δ 7.21–7.64 (m, 4H, aryl-H); 6.43 (s, 1H, thiophene-H); 4.97 (s, 2H, CH$_2$-7-ring); 2.84 (t, J=8 Hz, 2H, CH$_2$-thiophene); 2.30 (t, J=8 Hz, 2H, N—CH$_2$); 2.72 (s, 3H, CH$_3$-triazole; 2.22 (s, 6H, N—(CH$_3$)$_2$), 1.81 (m, 2H, N—CH$_2$CH$_2$).

EXAMPLE 69

$^1$H-NMR (CDCl$_3$) δ ppm 7.22–7.58 (4H, m, aryl-H); 6.36 (1H, s, thiophene-H); 4.93 (2H, s, 7-ring-CH$_2$); 2.74 (2H, t, J=7 Hz, N—CH$_2$); 2.71 (3H, s, triazole-CH$_3$); 2.09–2.51 (6H, m, piperidine-CH$_2$, thiophene-CH$_2$); 1.12–1.83 (16H, m, piperidine CH$_2$/N—CH$_2$—(CH$_2$)$_5$).

EXAMPLE 71

$^1$H-NMR (CDCl$_3$): δ 7.21–7.60 (m, 4H, aryl-H), 6.39 (s, 1H, thiophene H); 4.93 (s, 2H, CH$_2$-7-ring); 2.79 (t, J=8 Hz, 2H, CH$_2$-thiophene); 2.69 (s, 3H, CH$_3$-triazole); 2.52 (qu, J=7 Hz, 4H, N—(CH$_2$CH$_2$); 2.54 (t, J=7 Hz, 2H, CH$_2$-thiophene); 1.83 (m, 2H, N—CH$_2$CH$_2$); 0.98 (t, J=8 Hz, 6H, N—CH$_2$CH$_3$).

EXAMPLE 72

$^1$H-NMR (CDCl$_3$): δ 7.22–7.63 (m, 6H, aryl-H, pyrazole H 3/5); 6.38 (s, 1H, thiophene-H); 6.22 (t, J=2 Hz, 1H, pyrazole H 4); 4.94 (s, 2H, CH$_2$-7-ring); 4.17 (t, J=6 Hz, 2H, N—CH$_2$); 2.78 (t, J=6 Hz, 2H, CH$_2$-thiophene; 2.71 (s, 3H, CH$_3$-triazole); 2.26 (m, 2H, NCH$_2$CH$_2$—).

EXAMPLE 73

$^1$HNMR (CDCl$_3$); δ 7.22–7.66 (m, 6H, aryl-H, pyrazole H 3/5); 6.39 (s, 1H, thiophene-H); 6.25 (t, J=2 Hz, 1H, pyrazole-H4); 4.97 (s, 2H, CH$_2$-7-ring); 4.15 (t, J=7 Hz, 2H, N—CH$_2$); 2.78 (t, J=7 Hz, 2H, CH$_2$-thiophene); 2.72 (s, 3H, CH$_3$ triazole); 1.08–2.05 (m, 10H, N—CH$_2$(CH$_2$)$_5$—).

EXAMPLE 74

$^1$H-NMR (CDCl$_3$): δ 7.29–7.62 (m, 4H, aryl-H); 6.67 (t, J=2 Hz, 2H, pyrrole-H 2/5); 6.39 (s, 1H, thiophene-H); 6.16 (t, J=2 Hz, 2H, pyrrol-H/3/4); 4.98 (s, 2H, CH$_2$-7-ring); 3.91 (t, J=7 Hz, 2H, N—CH$_2$); 2.72 (t, J=7 Hz, 2H, CH$_2$-thiophene); 2.72 (s, 3H, CH$_3$-triazole); 1.07–2.06 (m, 10 H, N—CH$_2$(CH$_2$)$_5$.

EXAMPLE 77

$^1$H-NMR (CDCl$_3$): δ 8.32 (s, 1H, NH-indole); 7.00–7.76 (m, 9H, aryl-H, indol-H); 6.35 (s, 1H, thiophene-H); 4.93 (s, 2H, CH$_2$-7-ring); 3.09 (s, 2H, CH$_2$CH$_2$N); 2.68 (s, 3H, CH$_3$ triazole); 2.45–2.94 (m, 4H, thiophene CH$_2$CH$_2$N—), 1.07–1.92 (m, 11H, N—CH$_2$(CH$_2$)$_5$—, NH).

EXAMPLE 81

$^1$H-NMR (CDCl$_3$): δ 7.26–7.67 (4H, m, aryl-H); 6.47 (1H, s, thiophene-H); 4.96 (2H, s, CH$_2$-7-Ring); 4.35 (1H, m, X-part of ABX-System, OCH); 4.08, 3.63 (2H, m, AB-part of ABX-System, OCH$_2$); 3.02 (2H, d, J=7 Hz, CH$_2$-thiophene); 2.72 (3H, s, CH$_3$-triazozole); 1.43, 1.37 (6H, 2 s, C(CH$_3$)$_2$).

EXAMPLE 82

1H-NMR (CDCl$_3$): δ 7.11–7.71 (4H, m, aryl-H); 6.46 (1H, s, thiophene-H; 4.88 (2H, s, CH$_2$-7-ring; 4.10 (2H, s. broad, 2 OH); 3.33–4.07 (3H, m, ABX-System, OCH$_2$—CH—O); 2.92 (2H, d, J=5 Hs, CH$_2$-thiophene); 2.65 (3H, s, CH$_3$-triasole).

EXAMPLE 83b $^1$H-NMR (CDCl$_3$): δ 7.03–7.62 (9H, m, aryl-H); 6.46 ($^1$H, s, (thiophene-H); 5.00, 4.87 (2H, AB-system, J$_{AB}$=15 Hz, CH$_2$-ring); 4.10 (2H, m, OCH$_2$); 2.93 (3H, s, CH$_3$SO$_2$); 2.70 (3H, s, CH$_3$ triazole); 2.81 (4H, m, CH$_2$ aryl, CH$_2$ thiophene); 2.35 ($^1$H, m, —CH—).

EXAMPLE 83d $^1$H-NMR (CDCl$_3$): δ 6.67–7.60 (9H, m, aryl-H); 6.42 (1H, s, thiophene-H); 4.91 (2H, s, CH$_2$-7-ring); 3.98 (2H, t, J=6 Hz, OCH$_2$); 2.98 (2H, t, J=6 Hz, CH$_2$-thiophene); 2.65 (3H, s, CH$_3$-triazole); 2.11 (2H, m, =CH$_2$CH$_2$—).

EXAMPLE 83e $^1$H-NMR (CDCl$_3$): δ 7.27–7.58 (4H, m, aryl-H); 6.41 (1H, s, thiophene-H); 4.95 (2H, s, CH$_2$-7-ring); 3.39 (2H, t, J=6 Hz, OCH$_2$); 3.31 (3H, s, OCH$_3$); 2.87 (2H, t, J=6 Hz, CH$_2$-thiophene); 2.71 (3H, s, CH$_3$-triazole); 1.90 (2H, m, OCH$_2$CH$_2$).

EXAMPLE 83f $^1$H-NMR (CDCl$_3$): δ 8.31 (1 H, s, broad, NH); 6.95–7.70 (9H, m, aryl-indolyl-H); 6.32 (1H, s, thiophene-H); 4.90 (2H, s, CH$_2$-7-ring); 2.95 (4H, s, NHCH$_2$CH$_2$); 2.66 (3H, s, CH$_3$-triazole); 2.52–2.92 (4H, m, NHCH$_2$, CH$_2$-thiophene); 1.82 (2H, m, NH—CH$_2$CH$_2$).

EXAMPLE 83g $^1$H-NMR (CDCl$_3$): δ 6.25 (2H, s, 2-aryl-H); 6.78 (1H, s, thiophene-H); 4.85 (2H, s, CH$_2$-7-ring); 4.16 (2H, t, J=6 Hz, OCH$_2$); 3.86; 3.89 (9H, 2s, OCH$_3$); 2.95 (2H, t, J=6 Hz, CH$_2$-thiophene); 2.72 (3H, s, CH$_3$-triazole); 2.07 (3H, s, CH$_3$—C=O); 2.06 (2H, m, OCH$_2$CH$_2$—).

EXAMPLE 98

$^1$H-NMR (CDCl$_3$) δ ppm 7.15–7.59 (4H, m, aryl-H); 6.14 (1H, s, thiophene-H); 5.60 (s, 1H, CH—N), 4.14 (s, 2H, CH$_2$-7-ring), 3.67 (t, J=7Hz, 2H, OCH$_2$), 2.80 (t, J=7Hz, 2H, CH$_2$-thiophene), 2.70 (s, 3H, CH$_3$ triazole), 1.58–2.24 (m, 4H, OCH$_2$CH$_2$, NH, OH).

EXAMPLE 99

$^1$H-NMR (CDCl$_3$) δ ppm 7.16–7.58 (m, 4H, aryl-H), 6.14 (s, 1H, thiophene-H), 5.61 (s, 1H, CH—N), 4.14 (s, 2H, CH$_2$-7-ring), 4.08 (t, J=7Hz, OCH$_2$), 2.80 (t, J=7Hz, 2H, CH$_2$-thiophene), 2.71 (s, 3H, CH$_3$-triazole), 2.14 (s, broad, 1H, NH), 2.03 (s, 3H, CH$_3$CO), 1.96 (m, 2H, OCH$_2$CH$_2$).

EXAMPLE 100

$^1$H-NMR (CDCl$_3$) δ ppm 7.00–7.52 (m, 4H, aryl-H,), 7.07 (s, 1H, thiophene-H), 6.56 (s, 1H, CH—N), 4.93/4.70 (AB-system, J$_{AB}$=15Hz, 2H, CH$_2$-7-ring), 4.12 (t, J=6Hz, 2H, OCH$_2$), 2.87 (t, J=6Hz, 2H, thiophene-CH$_2$), 2.61 (s, 3H, CH$_3$-triazole), 2.28 (s, 3H, CH$_3$CO N), 2.07 (s, 3H, CH$_3$CO O), 1.98 (m, 2H, OCH$_2$CH$_2$).

Table 10 lists the NMR spectra of selected intermediate compounds.

TABLE 10

Compound No. 1

$^1$H-NMR (CDCl$_3$) δ ppm 7.29–7.54 (4H, m, aryl-H); 7.10 (2H, s, broad, NH$_2$); 6.17 (1H, s, thiophene-H); 3.75 (4H, m, morpholine-OCH$_2$); 3.24 (4H, m, morpholine-N-CH$_2$); 3.06 (4H, s, SO$_2$—CH$_2$—CH$_2$).

Compound No. 3

$^1$H-NMR (CDCl$_3$) δ ppm 7.33–7.78 (5H, m, aryl-H); 6.97 (2H, s, broad, NH$_2$); 6.56 (1H, s, thiophene-H); 4.09 (2H, t, J=6 Hz, OCH$_2$); 2.66 (2H, t, J=7 Hz, thiophene-CH$_2$); 2.04 (3H, s, CH$_3$C=O); 1.89 (2H, m, —O—CH$_2$CH$_2$—).

Compound No. 5

$^1$H-NMR (CDCl$_3$) δ ppm 7.24–7.49 (4H, m, aryl-H); 7.07 (2H, s, broad, NH$_2$); 6.09 (1H, s, thiophene-H); 4.05 (2H, t, J=7 Hz, OCH$_2$); (2H, t, J=7 Hz, thiophene-CH$_2$); 2.05 (3H, s, CH$_3$C=O); 1.08–1.83 (10H, m, OCH$_2$—(CH$_2$)$_5$).

Compound No. 5a $^1$H-NMR (CDCl$_3$): δ 6.93 (s, 2H, aryl-H); 6.64 (s, 1H, thiophene-H); 3.91; 3.92 (2 s, 9H, 3 OCH$_3$); 3.71 (t, J=7 Hz, 2H, OCH$_2$); 2.72 (t, J=7 Hz, 2H, thiophene-CH$_2$; 1.85 (m, 2H, OCH$_2$CH$_2$); NH$_2$ and OH very broad.

Compound No. 5b $^1$H-NMR (CDCl$_3$): δ 6.89 (s, 2H, aryl-H); 6.59 (s, 1H, thiophene-H); 4.09 (t, J=7 Hz, 2H, OCH$_2$); 3.90; 3.89 (2s, 9H, 3-OCH$_3$); 2.66 (t, J=7 Hz, 2H, thiophene-CH$_2$); 2.03 (s, 3H, CH$_3$C=O); 1.88 (m, 2H, OCH$_2$—CH$_2$); NH$_2$ very broad.

Compound No. 5c $^1$H-NMR (CDCl$_3$) δ ppm 7.19–7.52 (m, 4H, aryl-H), 7.07 (s, broad, 2H, NH$_2$), 6.18 (s, 1H, thiophene-H), 3.16–3.96 (m, 3H, OCH$_2$—CH), 2.67 (d, J=6Hz, CH$_2$-thiophene), 2.51 (d, J=3Hz, 1H, CHOH), 2.19 (t, J=4Hz, 1H, CH$_2$OH).

Compound No. 5d $^1$H-NMR (CDCl$_3$) δ ppm 7.09–7.67 (m, 9H, aryl-H), 6.97 (s, broad, 2H, NH$_2$), 6.19 (t, J<1Hz, 1H, thiophene-H), 5.93, 5.79 (2s, 1H, O—CH—O), 3.56–4.53 (m, 3H, OCH$_2$CH), 2.88 (dd, J=6Hz,<1Hz, 2H, thiophene-CH$_2$).

Compound No. 6

$^1$H-NMR (CDCl$_3$) δ ppm 12.60 (1H, s, broad, NH); 7.24–7.61 (4H, m, aryl-H); 6.53 (1H, s, thiophene-H); 4.13 (2H, s, CH$_2$Br); 3.68 (4H, m, morpholine-OCH$_2$); 3.23 (4H, m, morpholine-N-CH$_2$); 3.17 (4H, s, SO$_2$CH$_2$CH$_2$—).

Compound No. 7

$^1$H-NMR (CDCl$_3$) δ ppm 12.70 (1H, s, broad, NH); 7.34–7.62 (5H, m, aryl-H); 6.84 (1H, s, thiophene-H); 4.11 (2H, s, CH$_2$Br); 4.11 (2H, t, J=7 Hz, OCH$_2$); 2.82 (2H, t, J=7 Hz, thiophene-CH$_2$-); 2.04 (3H, s, CH$_3$G—C=O); 1.98 (2H, m, —OCH$_2$CH$_2$—).

Compound No. 8

$^1$H-NMR (CDCl$_3$): δ ppm 12.66 (1H, s, broad, NH); 7.33–7.61 (4H, m, aryl-H); 6.46 (1H, s, thiophene-H); 4.14 (2H, s, CH$_2$Br); 4.08 (2H, t, J=7 Hz, OCH$_2$); 2.78 (2H, t, J=7 Hz, thiophene-CH$_2$); 2.03 (3H, s, CH$_3$C=O); 1.93 (2H, m, OCH$_2$—CH$_2$—).

Compound No. 9

$^1$H-NMR (CDCl$_3$) δ ppm 12.64 (1H, s, broad, NH); 7.31–7.44 (4H, m, aryl-H); 6.41 (1H, s, thiophene-H); 4.14 (2H, s, CH$_2$Br); 4.05 (2H, t, J=6 Hz, OCH$_2$); 2.68 (2H, t, J=6 Hz, thiophene-CH$_2$); 2.04 (3H, s, CH$_3$C=O); 1.02–1.83 (10H, m, OCH$_2$(CH$_2$)$_5$—).

Compound No. 9d $^1$H-NMR (CDCl$_3$): δ 12.56 (1H, s, NH); 7.18–7.56 (4H, m, aryl-H); 6.48 (1H, s, thiophene H); 4.11 (2H, s, CH$_2$Br); 3.45–4.47 (3H, m, OCH$_2$—CHO); 2.90 (2H, d, J=6 Hz, CH$_2$-thiophene); 1.40; 1.31 (6H, 2 s, 2CH$_3$).

Compound No. 11

$^1$H-NMR (CDCl$_3$) δ ppm 13.10 (1H, s, broad, NH—C=O); 7.30–7.86 (5H, m, aryl-H); 6.80 (1H, s, thiophene-H); 4.11 (2H, t, J=7 Hz, OCH$_2$); 3.64 (2H, s, CH$_2$C=); 2.81 (2H, t, J=7 Hz, thiophene-CH$_2$); 2.04 (3H, s, CH$_3$C=O); 2.00 (2H, m, OCH$_2$CH$_2$—); 1.73 (2H, s, broad, NH$_2$).

Compound No. 12

$^1$H-NMR (CDCl$_3$) δ ppm 12.24 (1H, s, broad, NH); 7.25–7.56 (4H, m, aryl-H); 6.41 (1H, s, thiophene-H); 4.07 (2H, t, J=6 Hz, OCH$_2$); 3.67 (2H, s, CH$_2$C=O); 2.74 (2H, t, J=6 Hz, thiophene-CH$_2$); 2.00 (3H, s, CH$_3$C=O); 1.92 (2H, m, OCH$_2$CH$_2$—); 1.78 2H, s, broad, NH$_2$).

Compound No. 13

$^1$H-NMR (CDCl$_3$) δ ppm 13.60 (1H, s, broad, NH); 7.16–7.54 (4H, m, aryl-H); 6.38 (1H, s, thiophene-H), 4.04 (2H, t, J=6 Hz, OCH$_2$); 3.66 (2H, s, CH$_2$—C=O); 2.65 (2H, t, J=6 Hz, thiophene-CH$_2$); 1.87 (2H, s, broad, NH$_2$); 2.04 (3H, s, CH$_3$C=O); 1.23–1.72 (10H, m, OCH$_2$—(CH$_2$)$_5$—).

Compound No. 14

$^1$H-NMR (CDCl$_3$) δ ppm 9.29 (1H, s, broad, NH); 7.29–7.56 (4H, m, aryl-H); 6.31 (1H, s, thiophene-H); 4.48 (2H, s, 7-ring-CH$_2$); 3.75 (4H, m, morpholine-OCH$_2$); 3.23 (4H, m, morpholine-N-CH-hd 2); 3.14 (4H, s, —SO$_2$—CH$_2$—CH$_2$).

Compound No. 17

$^1$H-NMR (CDCl$_3$) δ ppm 10.03 (1H, s, broad, NH); 7.17–7.56 (4H, m, aryl-H); 6.16 (1H, s, thiophene-H); 4.47 (2H, s, 7-ring-CH$_2$); 4.02 (2H, t, J=6 Hz, OCH$_2$); 2.62 (2H, t, J=6 Hz, thiophene-CH$_2$); 2.02 (3H, s, CH$_3$—C=O); 1.03–1.82 (10H, m, OCH$_2$—(CH$_2$)$_5$).

Compound No. 17

$^1$H-NMR (CDCl$_3$): δ 9.33 (1H, s, broad, NH); 7.18–7.56 (4H, m, aryl-H); 6.25 (1H, s, thiophene-H); 4.46 (2H, s CH$_2$-7-ring); 3.45–4.37 (3H, m, OCH$_2$—CH—O); 2.88 (2H, d, J=6 Hz), CH$_2$-thiophene); 1.40; 1.32 (6H, 2 s, 2CH$_3$).

Compound No. 17d $^1$H-NMR (CD$_3$OD/CDCl$_3$ 1:1): δ 7.42 (4H, s, aryl-H); 6.29 (1H, s, thiophene-H); 4.35 (2H, s, CH$_2$-7-ring); 3.53–3.87 (1H, m, CH—O); 3.45 (2H, d, J=5 Hz, OCH$_2$); 2.52 (2H, m, CH$_2$-thiophene); NH, OH, is the solvent blind peak.

What we claim is:

1. A thieno-1,4-diazepine having the following structure

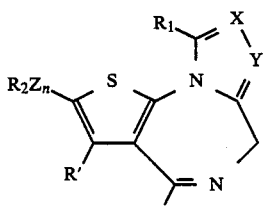

or

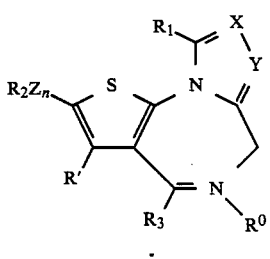

wherein
R$_1$ is hydrogen, branched or unbranched C$_1$-C$_4$ alkyl which may optionally be substituted by hydroxy or halogen, a cyclopropyl group, branched or unbranched C$_1$-C$_4$ alkoxy or a halogen, and
n is an integers from 0 to 10 and
when n is greater than zero,
R$_2$ is halogen hydroxy,

wherein
R$_4$ and R$_5$, which may be identical or difference, are hydrogen, branched or unbranched C$_1$-C$_{10}$ alkyl, alkenyl or alkynyl group with 2 to 10 carbon atoms which may optionally be substituted by halogen, hydroxy, morpholino or a c-linked heterocyclic group selected from the groups furan or indol, whilst the carbon chain may be interrupted by nitrogen, oxygen, oxygen or sulphur,
branched or unbranched C$_1$-C$_6$ alkylcarbonyl group, optionally substituted by hydroxy or halogen, or substituted by an amino group which is optionally mono- or di-substituted by branched or unbranched C$_1$-C$_6$ alkyl, whilst the alkyl group may be substituted by halogen or hydroxy, phenylcarbonyl, optionally substituted phenylsulphonyl or tolylsulphonyl, wherein the substituents are halogen, C$_1$-C$_4$ alkyl, hydroxy, C$_1$-C$_4$ alkoxy, amino or acetylamino, an alkylsulphonyl group with 1 to 4 carbon atoms, or R$_4$ and R$_5$ together with the nitrogen atom form a saturated or unsaturated 5-, 6- or 7-membered ring optionally mono- or polysubstituted by branched or unbranched alkyl groups with 1 to 4 carbon atoms, this ring possibly containing nitrogen, oxygen or sulphur as further heteroatoms, such as morpholin, piperazin, imidazol, 1,2,3-triazol, 1,2,4-triazol, pyrazol, imidazolin, imidazolidin, pyrazolin, pyrozolidin, thiomorpholin, or pyrrolidin, imidazol whilst each additional nitrogen atom may optionally be substituted by a branched or unbranched alkyl group with 1 to 4 carbon atoms,;

R$_2$ is an tolylsulphonyloxy or phenylsulphonyloxy, optionally mono- or polysubstituted by branched or unbranched C$_1$-C$_4$ alkyl or C$_1$-C$_4$ alkoxy groups with 1 to 4 carbon atoms;

R$_2$ is a branched or unbranched C$_1$-C$_4$ alkylsulphonyloxy group with 1 to 4 carbon atoms;

R$_2$ is phenylcarbonyloxy, optionally mono- or polysubstituted by branched or unbranched C$_1$-C$_4$ alkyl or C$_1$-C$_4$ alkoxy groups with 1 to 4 carbon atoms;

R$_2$ is branched or unbranched C$_1$-C$_{12}$ alkylcarbonyloxy group, whilst the alkyl chain may be interrupted by nitrogen, oxygen or sulphur;

R$_2$ is

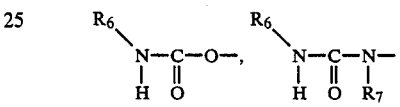

wherein
R$_6$ is branched or unbranched C$_1$-C$_4$ alkyl, alkenyl or alkynyl optionally substituted by halogen, an aryl group optionally mono- or polysubstituted by branched or unbranched C$_1$-C$_4$ alkyl or C$_1$-C$_4$ alkoxy
R$_7$ is hydrogen or branched or unbranched C$_1$-C$_4$ alkyl
R$_2$ is

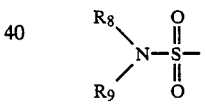

wherein R$_8$ and R$_9$, which may be identical or different, are branched or unbranched C$_1$-C$_4$ alkyl or R$_8$ and R$_9$ together with the nitrogen atom represent a 5- or 6-membered ring optionally mono- or polysubstituted by branched or unbranched C$_1$-C$_4$ alkyl groups with 1 to 4 carbon atoms, this group optionally containing as further heteroatoms nitrogen, oxygen or sulphur, such as morpholin, piperazin, triazol, pyrazol, imidazolin, imidazolidin, pyrazolin, pyrazolidin, thiomorpholin, pyrrolidin, or imidazol, whilst each additional nitrogen atom is substituted by C$_1$-C$_4$ alkyl
R$_2$ is branched or unbranched C$_1$-C$_4$ alkoxy group with 1 to 4 carbon atoms or phenyloxy optionally substituted by halogen, hydroxy, C$_1$-C$_4$ alkyl or C$_1$-C$_4$ alkoxy;
R$_2$ is an imido group dioxolan optionally substituted by methyl or phenyl
when n is greater than or equal to 0
R$_2$ is —CH=O, —COOH, of cyano;
R$_2$ is branched or unbranched C$_1$-C$_4$ alkoxycarbonyl with the proviso that if R' is hydrogen, R$_3$ is ochlorophenyl, X and Y both are nitrogen, R$_2$Z$_n$ cannot be methoxycarbonylethyl;

R2 is an aryloxycarbonyl group, preferably phenyloxycarbonyl;

R2 in the case that X and Y are not both nitrogen is a group of general formula

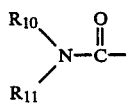

wherein

R10 and R11, which may be identical or different, are hydrogen, phenyl optionally substituted by halogen, $C_1$–$C_4$ alkyl, $C_1$–$C_4$ alkoxy or hydroxy, branched or unbranched $C_1$–$C_{10}$ alkyl $C_2$–$C_{10}$ alkenyl or alkynyl which may optionally be substituted by halogen, hydroxy, nitro, amino, substituted amino, or R10 and R11 are saturated or unsaturated 5-, 6- or 7-membered heterocyclic ring linked by a carbon atom, optionally mono- or polysubstituted by branched or unbranched $C_1$–$C_4$ alkyl R10 and R11 together with the nitrogen atom are a saturated or unsaturated 5-, 6- or 7-membered ring optionally mono- or polysubstituted by branched or unbranched $C_1$–$C_4$ alkyl and optionally containing, as further heteroatoms, nitrogen, oxygen, or sulphur, such as morpholin, piperazin, triazol, pyrazol, imidazolin, pyrazolin, pyrazolidin, imidazolidin, thiomorpholin, pyrrolidine, or imidazol, whilst each additional nitrogen atom may be substituted by branched or unbranched $C_1$–$C_4$ alkyl R2 is a group of general formula

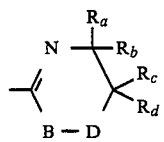

wherein

B is oxygen, sulphur, NH or $NC_1$–$C_6$-alkyl

D is the group (C Re Rf)n', wherein n may be an integer from 0 to 3,

Ra is hydrogen, $C_1$–$C_6$ alkyl optionally substituted by hydroxy or $C_1$ to $C_4$ alkoxycarbonyl, dialkylaminocarbonyl, Rb, Rc, Rd, Re, Rf are each hydrogen, $C_1$–$C_6$ alkyl optionally substituted by a hydroxy or amino group, or phenyl;

R3 is phenyl, wherein the phenyl ring, preferably in the 2 position, may be mono or poly-substituted by methyl, halogen, nitro, alkoxy, or trifluoromethyl, or R3 is pyridyl, R is hydrogen, alkyl or an acyl group with 1 to 4 carbon atoms in the alkyl chain,;

R' is hydrogen, phenyl optionally substituted by halogen, hydroxy, $C_1$–$C_4$ alkyl, or $C_1$–$C_4$ alkoxy, or R' is branched or unbranched $C_1$–$C_4$ alkyl X,Y independently of each other are C—$R_1$ or N but cannot both simultaneously represent C—$R_1$, or Y is the group C—COOR*, wherein R* is alkyl or hydrogen, and X is nitrogen;

Z is a branched or unbranched alkyl or alkenyl group with n carbon atoms, wherein Z may optionally be substituted phenyl substituted by halogen, hydroxy, $C_1$–$C_4$ alkyl, or $C_1$–$C_4$ alkoxy or disubstituted by R2, whilst R2 may be identical or different;

in the form of its racemates, enantiomers, diastereomers and mixtures thereof, as a free base or as a physiologically acceptable acid addition salt thereof.

2. A compound of the formula Ia or Ib as claimed in claim 1, wherein

R1 is hydrogen, methyl, ethyl, methoxy, ethoxy or halogen;

R2 is chlorine, bromine, iodine or hydroxy,

wherein

R4 and R5, which may be identical or different, are each hydrogen, a branched or unbranched alkyl group with 1 to 6 carbon atoms, whilst the carbon chain may be interrupted by nitrogen, a branched or unbranched alkylcarbonyl group with 1 to 4 carbon atoms, optionally substituted by a dimethylamino group, a phenylcarbonyl group, and when R5 is hydrogen, R2 may also be a phenylsulphonyl group optionally substituted by acylamino, or R4 and R5 together with the nitrogen atom between them form a piperidine, pyrrolidine, N'-methyl-piperazine, an optionally dimethyl-substituted morpholine ring, a pyrrole, pyrazole, imidazole or triazole ring;

R2 is —CH=O; —COOH;

a Δ²-imidazoline, -oxazoline, -thiazoline optionally mono- or polysubstituted by methyl; a tolylsulphonyloxy group; a methylsulphonyloxy group; a phenylcarbonyloxy group; an alkylcarbonyloxy group with 1 to 5 carbon atoms; a methoxy- or ethoxycarbonyl group;

R2 is

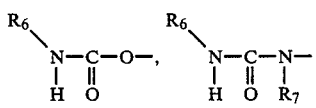

wherein R6 is branched or unbranched alkyl group with 1 to 4 carbon atoms, and R7 is hydrogen or a branched or unbranched alkyl group with 1 to 4 carbon atoms;

R2 is

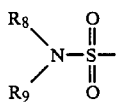

wherein R8 and R9, which may be identical or different, are each a methyl, ethyl, propyl or isopropyl group or R8 and R9 together with the nitrogen atom between them form an N'-methylpiperazine or morpholine ring;

R2 is

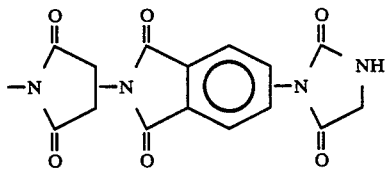

$R_3$ is phenyl, whilst the phenyl ring may be substituted by halogen;

R° is hydrogen, methyl or acetyl,

R' is hydrogen; and

Z is —(CH$_2$)$_n$—, optionally substituted by phenyl or disubstituted by $R_2$, whilst $R_2$ may also be different, or —CH$_2$—CHR$_2$—CH$_2$—R$_2$, —CH$_2$—CHR$_2$R$_2$, —CH$_2$CHR$_2$—CH$_2$—C$_6$H$_5$;

or a pharmaceutically acceptable acid addition salt thereof.

3. A compound of the formula Ia as claimed in claim 2, wherein $R_1$ is methyl or methoxy, $R_3$ is o-chlorophenyl, R' is hydrogen, X and Y are both nitrogen or X is C—H and Y is nitrogen, Z is —(CH$_2$)$_n$—, and n is the number 2, 3 or 7.

4. A pharmaceutical composition comprising a compound of formula Ia or Ib, as set forth in claim 1, and a pharmaceutically acceptable carrier.

5. A method of treating a pathological condition or disease in which PAF (platelet activating factor) is implicated in a warm-blooded animal which comprises administering to said animal a PAF-antagonizing amount of a compound as recited in claim 1.

6. A method for treating asthma is a warm-blooded animal which comprises administering to said animal a therapeutically effective amount of a compound as recited in claim 1.

* * * * *